(12) United States Patent
Smith et al.

(10) Patent No.: US 10,494,440 B2
(45) Date of Patent: Dec. 3, 2019

(54) USE OF SEMAPHORIN-4D BINDING MOLECULES TO PROMOTE NEUROGENESIS FOLLOWING STROKE

(71) Applicant: VACCINEX, INC., Rochester, NY (US)

(72) Inventors: Ernest S. Smith, W. Henrietta, NY (US); Maurice Zauderer, Pittsford, NY (US)

(73) Assignee: Vaccinex, Inc., Rochester, NY (US)

( * ) Notice: Subject to any disclaimer, the term of this patent is extended or adjusted under 35 U.S.C. 154(b) by 110 days.

(21) Appl. No.: 13/842,523

(22) Filed: Mar. 15, 2013

(65) Prior Publication Data

US 2013/0302320 A1    Nov. 14, 2013

Related U.S. Application Data

(60) Provisional application No. 61/646,119, filed on May 11, 2012.

(51) Int. Cl.
   *A61N 1/36*     (2006.01)
   *C07K 16/28*    (2006.01)
   *A61K 39/00*    (2006.01)

(52) U.S. Cl.
   CPC ...... *C07K 16/2896* (2013.01); *C07K 16/2803* (2013.01); *A61K 2039/505* (2013.01)

(58) Field of Classification Search
   None
   See application file for complete search history.

(56) References Cited

U.S. PATENT DOCUMENTS

| | | | |
|---|---|---|---|
| 5,070,192 A | 12/1991 | Earnshaw et al. |
| 5,595,756 A | 1/1997 | Bally et al. |
| 6,497,872 B1 | 12/2002 | Weiss et al. |
| 6,498,018 B1 | 12/2002 | Carpenter |
| 6,541,255 B1 | 4/2003 | Snyder et al. |
| 6,576,754 B2 | 6/2003 | Hall et al. |
| 6,635,742 B1 | 10/2003 | Boyle et al. |
| 6,638,501 B1 | 10/2003 | Bjornson et al. |
| 6,777,233 B2 | 8/2004 | Carpenter |
| 6,884,879 B1 | 4/2005 | Baca et al. |

(Continued)

FOREIGN PATENT DOCUMENTS

| EP | 1365018 A1 | 11/2003 |
|---|---|---|
| EP | 1442749 A1 | 8/2004 |

(Continued)

OTHER PUBLICATIONS

Shimada et al., Isolation of locally-derived stem/progenitor cells from the periinfarct area that do not migrate from the lateral ventricle after cortical stroke. Stroke. Sep. 2010 ; 41(9): e552-e560.*

(Continued)

*Primary Examiner* — Aurora M Fontainhas
(74) *Attorney, Agent, or Firm* — canady + lortz LLP

(57) ABSTRACT

Provided herein are methods for promoting neurogenesis in neural tissue of a patient exhibiting at least one symptom of a central nervous system disorder, the method comprising administering to a subject in need thereof an effective amount of an isolated binding molecule which specifically binds to semaphorin-4D (SEMA4D).

10 Claims, 8 Drawing Sheets

Figure 1:
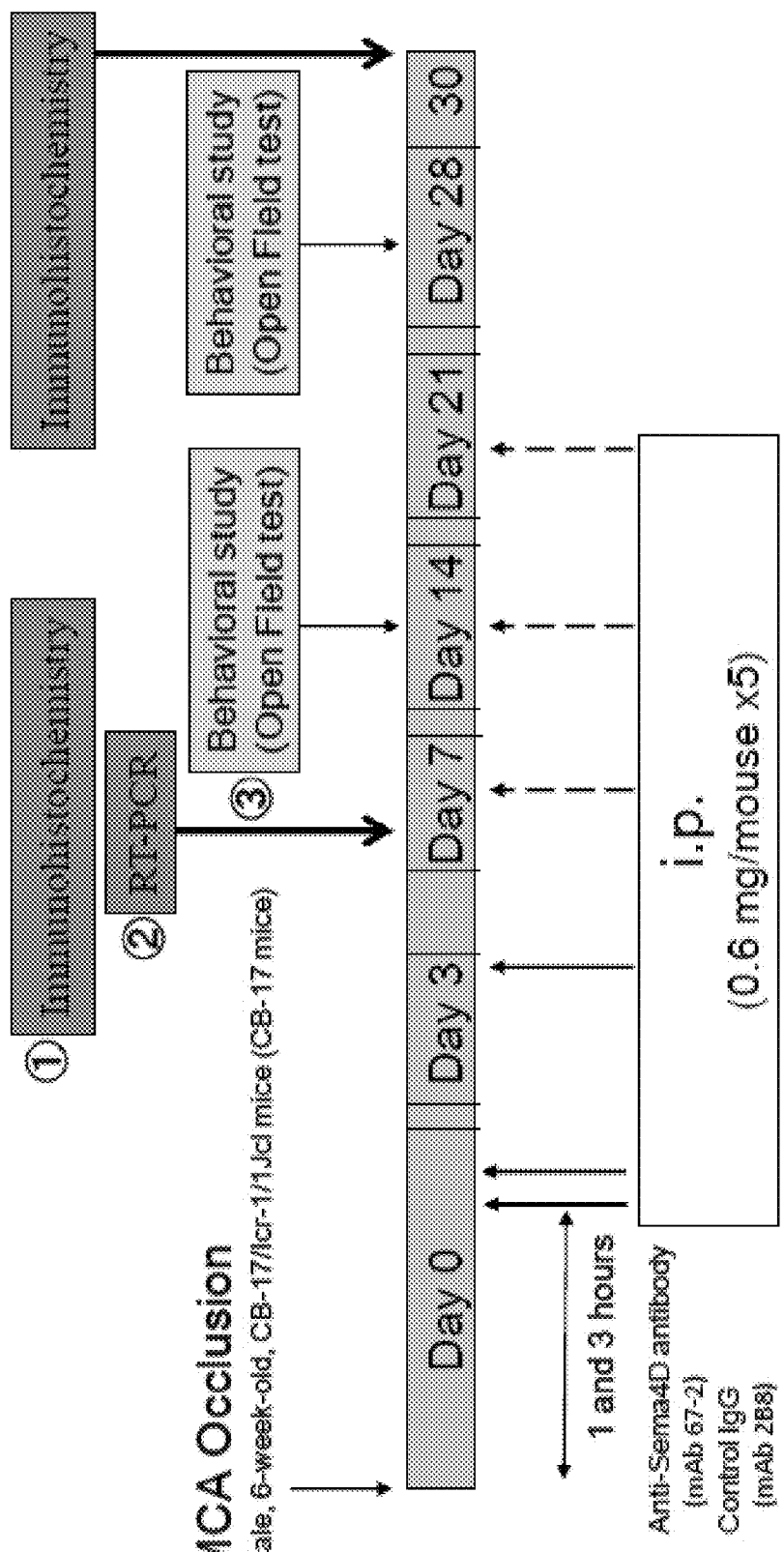

Specification includes a Sequence Listing.

(56) References Cited

U.S. PATENT DOCUMENTS

| | | | |
|---|---|---|---|
| 7,060,269 | B1 | 6/2006 | Baca et al. |
| 7,169,901 | B2 | 1/2007 | Baca et al. |
| 7,351,803 | B2 | 4/2008 | Johnson et al. |
| 7,407,766 | B1 | 8/2008 | Fujisawa et al. |
| 7,414,108 | B2 | 8/2008 | Laus et al. |
| 7,700,102 | B2 | 4/2010 | Hall et al. |
| 7,919,246 | B2 | 4/2011 | Lai et al. |
| 7,919,594 | B2 * | 4/2011 | Smith et al. ............. 530/387.3 |
| 8,067,247 | B2 | 11/2011 | Belin et al. |
| 8,496,938 | B2 | 7/2013 | Smith et al. |
| 8,790,652 | B2 | 7/2014 | Basile et al. |
| 8,816,058 | B2 | 8/2014 | Smith et al. |
| 9,090,709 | B2 | 7/2015 | Fisher et al. |
| 9,243,068 | B2 | 1/2016 | Evans et al. |
| 9,249,227 | B2 | 2/2016 | Smith et al. |
| 9,598,495 | B2 | 3/2017 | Smith et al. |
| 9,605,055 | B2 | 3/2017 | Smith et al. |
| 2002/0012903 | A1 | 1/2002 | Goldman et al. |
| 2002/0037851 | A1 | 3/2002 | Fleckenstein et al. |
| 2003/0158402 | A1 | 8/2003 | Hall et al. |
| 2005/0147612 | A1 | 7/2005 | Yayon et al. |
| 2006/0147449 | A1 | 7/2006 | Brass et al. |
| 2006/0233793 | A1 | 10/2006 | Belin et al. |
| 2007/0098707 | A1 | 5/2007 | Kong-Beltran et al. |
| 2007/0148177 | A1 | 6/2007 | Fyfe et al. |
| 2007/0154483 | A1 | 7/2007 | Fyfe et al. |
| 2008/0219971 | A1 | 9/2008 | Smith et al. |
| 2009/0104193 | A1 | 4/2009 | Lai et al. |
| 2009/0181035 | A1 | 7/2009 | Watts et al. |
| 2010/0040617 | A1 | 2/2010 | Brass et al. |
| 2010/0285036 | A1 | 11/2010 | Smith et al. |
| 2012/0027758 | A1 | 2/2012 | Belin et al. |
| 2012/0064035 | A1 | 3/2012 | Hadden et al. |
| 2012/0082663 | A1 | 4/2012 | Dennis et al. |
| 2012/0270268 | A1 | 10/2012 | Smith et al. |
| 2013/0095118 | A1 | 4/2013 | Smith et al. |
| 2013/0142810 | A1 | 6/2013 | Basile et al. |
| 2013/0274449 | A1 | 10/2013 | Smith et al. |
| 2013/0288927 | A1 | 10/2013 | Smith et al. |
| 2014/0072578 | A1 | 3/2014 | Smith et al. |
| 2014/0099334 | A1 | 4/2014 | Fisher et al. |
| 2014/0303358 | A1 | 10/2014 | Takayanagi |
| 2015/0044219 | A1 | 2/2015 | Evans et al. |
| 2015/0104462 | A1 | 4/2015 | Zauderer |
| 2015/0110800 | A1 | 4/2015 | Smith et al. |
| 2015/0353641 | A1 | 12/2015 | Smith et al. |
| 2016/0115240 | A1 | 4/2016 | Evans et al. |

FOREIGN PATENT DOCUMENTS

| | | |
|---|---|---|
| JP | 2001-157583 A | 6/2001 |
| JP | 2005-500034 A | 1/2005 |
| JP | 2007-308465 A | 11/2007 |
| WO | WO 93/14125 | 7/1993 |
| WO | 95/07706 A1 | 3/1995 |
| WO | 97/17368 A1 | 5/1997 |
| WO | 00/028016 A1 | 5/2000 |
| WO | WO 03/100041 A1 | 12/2003 |
| WO | 2004/067034 A1 | 8/2004 |
| WO | 2005/000900 A1 | 1/2005 |
| WO | 2006/110594 A2 | 10/2006 |
| WO | WO 2008/100995 A1 | 8/2008 |
| WO | WO 2010/129917 A1 | 11/2010 |
| WO | WO 2011/159704 A1 | 12/2011 |
| WO | 2012/157237 A1 | 11/2012 |
| WO | 2013/055922 A1 | 4/2013 |
| WO | 2013/148854 A1 | 10/2013 |
| WO | 2013/170221 A1 | 11/2013 |
| WO | 2014/209802 | 12/2014 |
| WO | 2015/054628 | 4/2015 |
| WO | 2015/061330 | 4/2015 |

OTHER PUBLICATIONS

Delaire, S., et al., "Biological Activity of Soluble CD100. II. Soluble CD100, Similarly to H-SemaIII, Inhibits Immune Cell Migration," *J. Immunol.* 166:4348-4354, The American Association of Immunologists, United States (2001).

Elhabazi, A., et al., "Biological Activity of Soluble CD100. I. The Extracellular Region of CD100 Is Released from the Surface of T Lymphocytes by Regulated Proteolysis," *J. Immunol.* 166:4341-4347, The American Association of Immunologists, Inc., United States (2001).

Giraudon, P., et al., "Semaphorin CD100 from Activated T Lymphocytes Induces Process Extension Collapse in Oligodendrocytes and Death of Immature Neural Cells," *J. Immunol.* 172:1246-1255, The American Association of Immunologists, Inc., United States (2004).

Giraudon, P., et al., "T-Cells in Neuronal Injury and Repair," *NeuroMolecular Medicine* 7:207-216, Humana Press, United States (2005).

Herold, C., et al., "Activation signals are delivered through two distinct epitopes of CD100, a unique 150 kDa human lymphocyte surface structure previously defined by BB18 mAb," *Int. Immunol.* 7(1):1-8, Oxford University Press, England (1994).

Ishida, I., et al., "Involvement of CD100, a lymphocyte semaphoring, in the activation of the human immune system via CD72: implications for the regulation of immune and inflammatory responses," *Int. Immunol.* 15(8):1027-1034, The Japanese Society for Immunology, Japan (2003).

Kikutani, H. and Kumanogoh, A., "Semaphorins in interactions between T cells and antigen-presenting cells," *Nat. Rev. Immunol.* 3(2):159-167, Nature Pub. Group, England (2003).

Kruger, R.P., "Semaphorins Command Cells to Move," *Nat. Rev. Mol. Cell Biol.* 6:789-800, Nature Pub. Group, England (2005).

Kumanogoh, A., "Identification of CD72 as a Lymphocyte Receptor for the Class IV Semaphorin CD100: A Novel Mechanism for Regulating B Cell Signaling," *Immunity* 13:621-631, Cell Press, United States (2000).

Kumanogoh, A. and Kikutani, H., "The CD100-CD72 interaction: a novel mechanism of immune regulation," *TRENDS in Immunology* 22(12):670-676, Elsevier Science Ltd., England (2001).

Kumanogoh, A., et al., "Requirement for the Lymphocyte Semaphorin, CD100, in the Induction of Antigen-Specific T Cells and the Maturation of Dendritic Cells," *J. Immunol.* 169:1175-1181, The American Association of Immunologists, United States (2002).

Pastercamp, R.J., "R-Ras fills another GAP in semaphoring signaling," *TRENDS in Cell Biology* 15(2):61-64, Elsevier Science Publishers, England (2005).

Shi, W., et al., "The Class IV Semaphorin CD100 Plays Nonredundant Roles in the Immune System: Defective B and T Cell Activation in CD100-Deficient Mice," *Immunity* 13:633-642, Cell Press, United States (2000).

Suzuki, K., et al., "Semaphorins and their receptors in immune cell interactions," *Nat. Immunol.* 9(1):17-23, Nature America Inc., United States (2008).

Taniguchi, Y., et al., "Sema4D deficiency results in an increase in the number of oligodendrocytes in healthy and injured mouse brains," *J. Neurosci. Res.* 87(13):2833-2841, Wiley Interscience, United States (2009).

Tamagnone, L., "Plexins Are a Large Family of Receptors for Transmembrane, Secreted, and GPI-Anchored Semaphorins in Vertebrates," *Cell* 99:71-80, Cell Press, United States (1999).

Wang, X., et al., "Functional soluble CD100/Sema4D released from activated lymphocytes: possible role in normal and pathologic immune responses," *Blood* 97:3498-3504, The American Society of Hematology, United States (2011).

Watanabe, C., et al., "Enhanced Immune Responses in Transgenic Mice Expressing a Truncated Form of the Lymphocyte Semaphorin CD100," *J. Immunol.* 167:4321-4328, The American Association of Immunologists, United States (2001).

Witherden, D.A., et al., "The CD100 Receptor Interacts with Its Plexin B2 Ligand to Regulate Epidermal γσ T Cell Function," *Immunity* 37(2):314-325, Cell Press, United States (2012).

(56) References Cited

OTHER PUBLICATIONS

Chabbert-de Ponnat, I., et al., "Soluble CD100 functions on human monocytes and immature dendritic cells require plexin C1 and plexin B1, respectively," Int. Immunol. 17(4):439-447, Oxford University Press, England (2005).
Fujioka, S., et al., "Neurotrophic effect of Semaphorin 4D in PC12 cells," Biochem. Biophys. Res. Commun. 301(2):304-310, Academic Press, United States (2003).
Moreau-Fauvarque, C., et al., "The Transmembrane Semaphorin Sema4D/CD100, an Inhibitor of Axonal Growth, is Expressed on Oligodendrocytes and Upregulated after CNS Lesion," J. Neurosci. 23(27):9229-9239, Society for Neuroscience, United States (2003).
International Search Report and Written Opinion for PCT/US2013/040661 dated Oct. 8, 2013.
Aagaard et al., "RNAi Therapeutics: Principles, Prospects and Challenges", Advanced Drug Delivery Reviews, Mar. 4, 2007, pp. 75-86, vol. 59.
Advisory Action for U.S. Appl. No. 12/776,187 dated Mar. 6, 2013.
Alberts et al., "The Generation of Antibody Diversity", Molecular Biology of the Cell—4th Edition, 2002, Garland Science, New York.
Argaw, A.T., et al., "VEGF-mediated disruption of endothelial CLN-5 promotes blood-brain barrier breakdown," PNAS 106(6): 1977-1982, The National Academy of Sciences of the USA, United States (2009).
Auerbach et al., "Angiogenesis Assays: Problems and Pitfalls", Cancer and Metastasis Reviews, 2000, pp. 167-172, vol. 19, Kluwer Academic Publishers.
Banks, W.A. et al., "The blood-brain barrier and immune function and dysfunction," Neurobiology of Disease 37:26-32, Elsevier Inc.(2010).
Basile et al, "Semaphorin 4D Provides a Link Between Axon Guidance Processes and Tumor-Induced Angiogenesis", Proceedings of the National Academy of Sciences, Jun. 2006, pp. 9017-9022, vol. 103 No. 24, National Academy of Sciences.
Beam, T.R. Jr. and Allen, J.C., "Blood, Brain, and Cerebrospinal Fluid Concentrations of Several Antibiotics in Rabbits with Intact and Inflamed Meninges," Antimicrobial Agents and Chemotherapy 12(6):710-716, American Society for Microbiology, United States (1977).
Billard et al., "Switch in the Protein Tyrosine Phosphatase Associated with Human CD 100 Semaphorin at Terminal B-Cell Differentiation Stage", Blood, Feb. 2000, pp. 965-972, vol. 95 No. 3, The American Society of Hematology, United States.
Bleck et al., "An Alternative Method for the Rapid Generation of Stable, High-Expressing Mammalian Cell Lines", Bioprocessing Journal, Sep.-Oct. 2005, pp. 36-42, vol. 5 No. 4, International Society for BioProcess Technology, United States.
Bork, "Powers and Pitfalls in Sequence Analysis: The 70% Hurdle", Genome Research, 2000, pp. 398-400, vol. 10, Cold Spring Harbor Laboratory Press.
Bougeret et al, "Increased Surface Expression of a Newly Identified 150-kDa Dimer Early After Human T Lymphocyte Activation" The Journal of Immunology, Jan. 1992, pp. 318-323, vol. 148 No. 2, The American Association of Immunologists, United States.
Bowie et al., "Deciphering the Message in Protein Sequences: Tolerance to Amino Acid Substitutions", Science, Mar. 16, 1990, pp. 1306-1310, vol. 247 No. 4948.
Brand et al., "Collagen-Induced Arthritis", Nature Protocols, May 2007, pp. 1269-1275, vol. 2 No. 5, Nature Publishing Group, England.
Brown et al., "Tolerance to Single, but Not Multiple, Amino Acid Replacements in Antibody VH CDR2: A Means of Minimizing B Cell Wastage from Somatic Hypermutation?", Journal of Immunology, May 1996, pp. 3285-3291 at 3290 and Tables 1 and 2, vol. 156 No. 9, The American Association of Immunologists.
Burgess, W. H, et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," The Journal of Cell Biology, 111:2129-2138, The Rockefeller University Press, United States (1990).
Bussolino, F., et al., "Molecular mechanisms of blood vessel formation," Trends Biochem. Sci. 22(7):251-256, Elsevier Trends Journals, England (1997).
Campos et al. "Ki-67 and CD 100 Immunohistochemical Expression is Associated with Local Recurrance and Poor Prognosis in Soft Tissue Sarcomas, Respectively", 2013 Oncology Letters pp. 1527-1535, vol. 5.
Carmeliet, P., "Angiogenesis in health and disease," Nat. Med. 9(6):653-660, Nature Publishing Company, United States (2003).
Ch'ng et al "Prognostic Signifigance of CD100 Expression in Soft Tissue Progression", Cancer, 2007, pp. 164-172 vol. 110, Issue 3.
Chen et al., "Generation and Analysis of Random Point Mutations in an Antibody CDR2 Sequence: Many Mutated Antibodies Lose their Ability to Bind Antigen", Journal of Experimental Medicine, Sep. 1992, pp. 855-866, vol. 176.
Cheung et al., "Age-Related Macular Degeneration", Pharmacotherapy, 2013, [Epub ahead of print], 18 pages.
Chodobski et al., "Blood-Brain Barrier Pathophysiology in Traumatic Brain Injury", Translational Stroke Research, Dec. 2011, pp. 492-516, vol. 2 No. 4.
Claesson-Welsh., "Novel Paths to Blood Vessel Formation", Blood, Jun. 2005, pp. 4153-4154, vol. 105 No. 11, The American Society of Hematology, United States.
Clark et al., "Discovery and Development of Janus Kinase (JAK) Inhibitors for Inflammatory Diseases", Journal of Medicinal Chemistry, Jan. 13, 2014, pp. 5023-5038, vol. 57, American Chemical Society.
Co-pending U.S. Appl. No. 14/511,679, filed Oct. 10, 2014, Inventor Zauderer, M. (Not Yet Published).
Co-pending U.S. Appl. No. 14/519,965, filed Oct. 21, 2014, Inventors Smith, E., Zauderer, M., Bowers, W., and Jonason, A. (Not Yet Published).
Co-pending U.S. Appl. No. 61/979,384, filed Apr. 14, 2014, Inventors Smith, E., Zauderer, M., Bowers, W., and Jonason, A. (Not Yet Published).
Co-pending U.S. Appl. No. 62/012,805, filed Jun. 16, 2014, Inventors Smith, E., Zauderer, M., Bowers, W., and Jonason, A. (Not Yet Published).
Colman et al., "Effects of Amino Acid Sequence Changes on Antibody-Antigen Interactions", Research in Immunology, 1994, 145:33-36.
Colton, C.A., et al., "The Effects of NOS2 Gene Deletion on Mice Expressing Mutated Human AbPP," J Alzheimers Dis. 15(4):571-587, IOS Press, Netherlands (2008).
Combes et al., "The Crossroads of Neuroinflammation in Infectious Diseases: Endothelial Cells and Astrocytes", Trends in Parasitology, Aug. 2012, pp. 311-319, vol. 28 No. 8.
Conrotto et al, "Sema4D Induces Angiogenesis Through Met Recruitment by Plexin B1", Blood, Jun. 2005, pp. 4321-4329, vol. 105 No. 11, The American Society of Hematology, United States.
Cucullo, L. et al. "A new dynamic in vitro model for the multidimensional study of astrocyte-endothelial cell interactions at the blood-brain barrier," Brain Research 951:243-254, Elsevier Science B.V. (2002).
Cucullo, L., et al., "A dynamic in vitro BBB model for the study of immune cell trafficking into the central nervous system," Journal of Cerebral Blood Flow & Metabolism 31:767-777, Nature Publishing Group, United States (2011), Epub. Sep. 15, 2010.
Cucullo, L., et al., "Development In Vitro Blood-Brain Barrier Model to Screen for Brain Penetration of Antiepileptic Drugs," Epilepsia 48(3):505-516, Blackwell Publishing, Inc., England (2007).
Curran et al, "Systemic 4-1BB Activation Induces a Novel T cell Phenotype Driven by High Expression of Eomesodermin", The Journal of Experimental Medicine 2013, pp. 743-755, vol. 210.
Dacquin et al., "Control of Bone Resorption by Semaphorin 4D is Dependent on Ovarian Function", PLOS One, Oct. 26, 2011, pp. e26627, vol. 6 No. 10.
Database GenBank, Apr. 18, 2005, Adams, "M.musculus mRNA for Semaphorin B", Data Accession No. X85991.

(56) References Cited

OTHER PUBLICATIONS

Database GenBank, Apr. 24, 1997, Hillier et al., "zt85a06.rl", Data Accession No. AA394007.
Database GenBank, Jan. 31, 1997, Strausberg, "zs16g08.rl", Date Accession No. AA262446.
De Pascalis et al., "Grafting of 'Abbreviated' Complementarity-Determining Regions Containing Specificity-Determining Residues Essential for Ligand Contact to Engineer a Less Immunogenic Humanized Monoclonal Antibody", Journal of Immunology, Sep. 15, 2002, pp. 3076-3084, vol. 169 No. 6.
Deaglio et al., "CD38 and CD100 Lead a Network of Surface Receptors Relaying Positive Signals for B-CLL Growth and Survival", Blood, Apr. 2005, pp. 3042-3050, The American Society of Hematology, United States.
Deane, R., et al., "LRP/Amyloid b-Peptide Interaction Mediates Differential Brain Efflux of Ab Isoforms," Neuron 43:333-344, Cell Press, United States (2004).
Delaire et al., "Inhibition of Immune Cell Migration by Soluble CD100 and H-Sema III Semaphorins", Tissue Antigens, 2000, pp. 103, vol. 55 No. 1, Wiley-Blackwell, England (Abstract Only).
Dougher, M: and Terman, B.I., "Autophosphorylation of KDR in the kinase domain is required for maximal VEGF-stimulated kinase activity and receptor internalization," Oncogene 18(8):1619-1627, Nature Publishing Group, England (1999).
Duran-Struuck et al., "A Novel Role for the Semaphorin Sema4D in the Induction of Allo-Responses", Biological Blood Marrow Transplant, Nov. 2007, pp. 1294-1303, vol. 13 No. 11.
Elhabazi et al., "Structure and Function of the Immune Semaphorin CD100/SEMA4D", Critical Review in Immunology, 2003, pp. 65-81, vol. 23 No. 1-2, Begell House, Inc. United States.
Elhabazi et al., "The Human Semaphorin-Like Leukocyte Cell Surface Molecule CD100 Associates with a Serine Kinase Activity", The Journal of Biological Chemistry, Sep. 1997, pp. 23515-23520, vol. 272 No. 38, The American Society for Biochemistry and Molecular Biology, Inc., United States.
Engelhardt et al., "Capture, Crawl, Cross: The T Cell Code to Breach the Blood-Brain Barriers", Trends in Immunology, Dec. 2012, pp. 579-589, vol. 33 No. 12.
Kleinschmidt-Demasters et al., "Update on PML and PML-IRIS Occurring in Multiple Sclerosis Patients Treated with Natalizumab", Journal of Neuropathology & Experimental Neurology, Jul. 2012, pp. 604-617, vol. 71 No. 7.
Kornbluth et al., "Novel Tyrosine Kinase Identified by Phosphotyrosine Antibody Screening of eDNA Libraries", Molecular and Cellular Biology, Sep. 1988, pp. 5541-5544, vol. 8 No. 12, American Society for Microbiology, United States.
Kortekaas, R., et al., "Blood-brain barrier dysfunction in parkinsonian midbrain in vivo." Ann. Neurol. 57:176-179, The American Neurological Association, United States (2005).
Kumanogoh et al., "Class IV Semaphorin Sema4A Enhances T-Cell Activation and Interacts with Tim-2", Nature, Oct. 2002, pp. 629-633, vol. 419 No. 6907, Nature Publishing Group, London.
Kumanogoh et al., "Immune Semaphorins: A New Area of Semaphorin Research", Journal of Cell Science, Sep. 2003, pp. 3463-3470, vol. 116, The Company of Biologists Ltd., United Kingdom.
Lamminmaki, U., and Kankare, J. A., "Crystal Structure of a Recombinant Anti-estradiol Fab Fragment in Complex with 17b-Estradiol," The Journal of Biological Chemistry 276(39):36687-36694, The American Society for Biochemistry and Molecular Biology, Inc., United States (2001).
Lazar, E., et al,, "Transforming Growth Factor a: Mutation of Aspartic Acid 47 and Leucine 48 Results in Different Biological Activities," Molecular and Cellular Biology 8(3):1247-1252, American Society for Microbiology, United States (1988).
Levin, M. C., et al., "Molecular Mimicry to Neurons Results in Neurological Disease," Abstract Viewer and Itinerary Planner: Program No. 415.3., Society of Neuroscience, United States (2002) (Abstract).
Li et al., "CD72 Down-Modulates BCR-Induced Signal Transduction and Diminishes Survival in Primary Mature B Lymphocytes", The Journal of Immunology, May 2006, pp. 5321-5328, vol. 176, The American Association of Immunologists, United States.
Li et al., "Modulation of Peripheral B Cell Tolerance by CD72 in a Murine Model", Arthritis and Rheumatism, Oct. 2008, pp. 3192-3904, vol. 58 No. 10, The American College of Rheumatology, United States.
Liddy et al, "Monoclonal TCR-Redirected Tumor Cell Killing", Nature Med. 2012, pp. 980-987, vol. 18.
Lizee et al, "Harnessing the Power of the immune system to target cancer", 2013, Annu rev med pp. 71-90, vol. 64.
Lochhead, J.J., et al., "Oxidative stress increases blood-brain barrier permeability and induces alterations in occludin during hypoxia-reoxygenation," Journal of Cerebral Blood Flow & Metabolism 30:1625-1636, Nature Publishing Group, United States (2010).
Love, C.A., et al., "The ligand-binding face of the semaphorins revealed by the high-resolution crystal structure of SEMA4D," Nat. Struct. Biol. 10:843-848, Nature Pub. Co., United States (2003).
Lu et al., "Targeting Metabolic Inflammation in Parkinson's Disease: Implications for Prospective Therapeutic Strategies", Clinical and Experimental Pharmacology and Physiology, 2012, pp. 577-585, vol. 39.
Lyketsos et al., "Neuropsychiatric Symptoms in Alzheimer's Disease", Alzheimer's & Dementia, Sep. 2011, pp. 1-14, vol. 7 No. 5.
Ma et al, Chemotherapy and Radiotherapy: Cryptic Anticancer Vaccines, Seminars in Immunology 2010, pp. 113-124, vol. 22, Issue 3.
MacCallum et al., "Antibody-Antigen Interactions: Contact Analysis and Binding Site Topography", J. Mol. Biol., 1996, pp. 732-745, vol. 262.
Machiels et al, "Cyclophosphamide, Doxorubicin, and Paclitaxel Enhance the Antitumor Immune Response of Granulocyte/Macrophage-Colony Stimulating Factor-secreting Whole-Cell Vaccines in HER-2/neu Tolerized Mice", Cancer Research, 2001, pp. 3689-3697, vol. 61.
Marco, S., et al., "Amyloid b-peptide 1-42 alters tight junction protein distribution and expression in brain microvessel endothelial cells." Neuroscience Letters 401:219•-224, Elsevier Ireland Ltd. (2006).
Maroso et al., "Toll-Like Receptor 4 and High-Mobility Group Box-1 are Involved in Ictogenesis and can be Targeted to Reduce Seizures", Nature Medicine, Apr. 2010, vol. 16 No. 4.
McAllister, M.S., et al., "Mechanisms of glucose transport at the blood-brain barrier: and in vitro study," Brain Research 904:20-30, Elsevier Science B.V. (2001).
Miller, S.D., et aL, "Experimental autoimmune encephalomyelitis in the mouse" Current Protocols in Immunology 15.1.1-15.1.18, John Wiley & Sons, Inc. (2007).
Minagar, A. and Alexander, J.S., "Blood-brain barrier disruption in multiple sclerosis," Multiple Sclerosis 9:540-549, Arnold, England (2003).
Mizrahi et al., "CD100 on NK Cells Enhance IFN[gamma] Secretion and Killing of Target Cells Expressing CD72", PLOS One, Jan. 2007, pp. e818, vol. 2 No. 9, New York University School of Medicine, United States.
Mogi et al., "Neurovascular Coupling in Cognitive Impairment Associated with Diabetes Mellitus", Circulation Journal, May 2011, pp. 1042-1048, vol. 75.
Negishi-Koga et al., "Suppression of bone formation by osteoclastic expression of semaphorin 4D", Nature Medicine, 2011, p. 1473-1480, vol. 17, No. 11.
Notice of Allowance for U.S. Appl. No. 12/776,187 dated Apr. 1, 2013.
Nuber et al., "Neurodegeneration and Motor Dysfunction in a Conditional Model of Parkinson's Disease", Journal of Neuroscience, Mar. 5, 2008, pp. 2471-2484, vol. 28 No. 10.
Oby, E. and Janigro, D., "The Blood-Brain Barrier and Epilepsy," Epilepsia 47(11): 1761-1774, Blackwell Publishing, Inc., England (2006).
Office Action for U.S. Appl. No. 12/776,187 dated May 18, 2012.
Office Action for U.S. Appl. No. 12/776,187 dated Sep. 14, 2012.
Office Action for U.S. Appl. No. 13/517,807 dated Dec. 26, 2013.
Office Action for U.S. Appl. No. 13/517,807 dated May 14, 2013.
Office Action for U.S. Appl. No. 13/517,807 dated Sep. 16, 2013.

(56) References Cited

OTHER PUBLICATIONS

Office Action for U.S. Appl. No. 13/649,651 dated Mar. 5, 2014.
Office Action for U.S. Appl. No. 13/649,651 dated Oct. 31, 2014.
Office Action for U.S. Appl. No. 13/707,299 dated Jul. 19, 2013.
Office Action for U.S. Appl. No. 13/707,299 dated Nov. 29, 2013.
Office Action for U.S. Appl. No. 13/828,506 dated Aug. 15, 2014.
Office Action for U.S. Appl. No. 14/310,848 dated Jan. 14, 2015.
Oinuma et al., "Semaphorin 4D/Plexin-B1-Mediated R-Ras GAP Activity Inhibits Cell Migration by Regulating beta-1 Integrin Activity", The Journal of Cell Biology, 2006, pp. 601-613, vol. 173 No. 801.
Okuno et al., "Roles of Sema4D-Plexin-B1 Interactions in the Central Nervous System for Pathogenesis of Experimental Autoimmune Encephalomyelitis", The Journal of Immunology, Dec. 2009, pp. 1499-1506, vol. 184, The American Association of Immunologists, United States.
Pander, J., et al., "Pharmacogenetics of EGFR and VEGF inhibition," Drug Discov. Today 12(23-24):1054-1060, Elsevier Science Ltd., England (2007).
Pardridge, "Receptor-Mediated Peptide Transport Through the Blood-Brain Barrier," Endocrin. Rev. 7:314-330, The Endocrine Society (1986).
Presta, L.G., et al., "Humanization of an anti-vascular endothelial growth factor monoclonal antibody for the therapy of solid tumors and other disorders," Cancer Res. 57(20):4592-4599, American Associate for Cancer Research, United States (2005).
Qualls and Murray CH10, Tumor Macrophages: Protective and Pathogenic Roles in Cancer Development, Curr Topics in Develop Biol 2011, pp. 309-328, vol. 94.
Ransohoff, R.M., et al., "Three or More Routes for Leukocyte Migration Into the Central Nervous System," Nature Rev. Immun. 3:569-581, Nature Publishing Group (2003).
Regev et al., "Semaphorin-4D (Sema-4D), the Plexin-B1 Ligand, is Involved in Mouse Ovary Follicular Development", Reproductive Biology and Endocrinology, 2007, pp. 5.
Riemer et al., "Matching of Trastuzumab (Herceptin) Epitope Mimics Onto the Surface of Her-2/neu—A New Method of Epitope Definition", Molecular Immunology, 2005, pp. 1121-1124, vol. 42.
Risau, W., "Mechanisms of angiogenesis," Nature 386(6626):671-674, Nature Publishing Group, England (1997).
Roberts et al., "Vaccinia Virus Morphogenesis and Dissemination", Trends in Microbiology, 2008, pp. 472-479, vol. 16 No. 10, Elsevier Trends Journals, England.
Rosenberg et al, "Adoptive Cell Transfer: A Clinical Path to Effective Cancer Immunotherapy" Nature Reviews Cancer 2008, pp. 299-308, vol. 8.
Roth et al., "The Many Faces of Semaphorins: From Development to Pathology", CMLS Cellular and Molecular Life Sciences, Oct. 27, 2008, pp. 649-666, vol. 66 No. 4.
Rudikoff et al., "Single Amino Acid Substitution Altering Antigen-Binding Specificity", Proceedings of the National Academy of Sciences, Mar. 1982, pp. 1979-1983, vol. 79, National Academy of Sciences United States.
Ruffell et al., "Differential Macrophage Programming in the Tumor Microenviroment", Trends in Immunology 2012, pp. 119-126, vol. 33 No. 3.
Sagare et al., "Neurovascular Dysfunction and Faulty Amyloid beta-Peptide Clearance in Alzheimer Disease", 2012, Cold Spring Harbor Perspectives in Medicine, pp. a011452, vol. 2.
Sanchez-Del-Rio et al., "Migraine Aura: New Information on Underlying Mechanisms", Current Opinion in Neurology, 2004, pp. 289-293, vol. 17.
Santaguida, S., et al.,"Side by side comparison between dynamic versus static models of blood-brain barrier in vitro: a permeability study," Brain Research 1109:1-•13, Elsevier B.V. (2006).
Sica et al, "macrophage polarization in tumor progression" Seminars in Cancer Biol. 2008, pp. 349-355, vol. 18.
Sierra et al., "Tumor Angiogenesis and Progression are Enhanced by Sema4D Produced by Tumor-Associated Macrophages", Journal of Experimental Medicine, Jul. 2008, pp. 1673-1685, vol. 205 No. 7, The Rockefeller University Press, United States.
Skolnick et al., "From Genes to Protein Structure and Function: Novel Applications of Computational Approaches in the Genomic Era", Trends in Biotechnology, Jan. 2000, pp. 34-39, vol. 18 No. 1, Elsevier Science Ltd., United States.
Small et al, "Immunotherapy of Hormone-Refrectory Prostate Cancer with Antigen-Loaded Dendritic Cells" Journal of Clinical Oncology, 2000, pp. 3894-3903, vol. 18.
Smith et al., "SEMA4D Compromises Blood-Brain Barrier, Activates Microglia, and Inhibits Remyelination in Neurodegenerative Disease", Neurobiology of Disease, Jan. 2015, pp. 254-268, vol. 73, Elsevier Inc.
Sporn et al., "Chemoprevention of Cancer", Carcinogenesis, 2000, pp. 525-530, vol. 21 No. 3, Oxford University Press.
Stamatovic, S.M. et al., "Inflammation and brain edema: new insights into the role of chemokines and their receptors," Acta Neurochirurgica, Supplement 96:444-450, Springer-Verlag, Austria (2006).
Stancovski et al., "Mechanistic Aspects of the Opposing Effects of Monoclonal Antibodies to the ERBB2 Receptor on Tumor Growth", Proceedings of the National Academy of Science USA, Oct. 1991, pp. 8691-8695, vol. 88.
Swiercz et al., "ErbB-2 and Met Reciprocally Regulate Cellular Signaling via Plexin-B1", The Journal of Biological Chemistry, Jan. 2008, pp. 1893-1901, vol. 283 No. 4, The American Society for Biochemistry and Molecular Biology, Inc., United States.
Takeuchi et al., "Angiogenesis in Primary Central Nervous System Lymphoma (PCNSL)", Journal of Neuro-Oncology, 2007, pp. 141-145, vol. 84.
Tamura et al., "Structural Correlates of an Anticarcinoma Antibody: Identification of Specificity-Determining Residues (SDRs) and Development of a Minimally Immunogenic Antibody Variant by Retention of SDRs Only", The Journal of Immunology, 2000, pp. 1432-1441, vol. 164.
Turner et al., "Plexin-Induced Collapse Assay in COS Cells", Methods in Enzymology, 2006, pp. 665-676, vol. 406, Elsevier Inc., United States.
U.S. Department of Health and Human Services, Food and Drug Administration, Center for Drug Evaluation and Research (CDER), Office of Orphan Products Development (OOPD), "Guidance for Industry—Interpreting Sameness of Monoclonal Antibody Products Under the Orphan Drug Regulations", Apr. 2014, pp. 1-6.
Unverified, machine-generated English language translation of the French Patent Publication No. FR 2686087 A1 (corresponds to International Patent Application No. WO 93/14125 A1), European Patent Office, espacenet database—Worldwide (1993) (equivalent of document FP1 cited on the accompanying form PTO/SB/08A).
Vajdos et al., "Comprehensive Functional Maps of the Antigen-binding Site of an Anti-ErbB2 Antibody Obtained with Shotgun Scanning Mutagenesis", Journal of Molecular Biology, Jul. 5, 2002, pp. 415-428 at p. 416, vol. 320 No. 2.
Van Nostrand, W.E., et al., "Enhanced Capillary Amyloid Angiopathy-Associated Pathology in Tg-SwDI Mice With Deleted Nitric Oxide Synthase 2," Stroke 41:S135-S138, American Heart Association, Inc., United States (2010).
Voet et al., Biochemistry, 1990, pp. 126-128 and pp. 228-234, Jon Wiley & Sons, Inc., United States.
Waikar et al., "Imperfect Gold Standards for Kidney Injury Biomarker Evaluation", Journal of the American Society of Nephrology, Jan. 2012, pp. 13-21, vol. 23 No. 1.
Warzocha et al., "Antisense Strategy: Biological Utility and Prospects in the Treatment of Hematological Malignancies", Leukemia and Lymphoma, May 12, 1996, pp. 267-281, vol. 24.
Waubant E., "Biomarkers indicative of blood-brain barrier disruption in multiple sclerosis," Disease Markers 22:235-244, IOS Press (2006).
Westin, J.E., et al., "Endothelial Proliferation and Increased Blood-Brain Barrier Permeability in the Basal Ganglia in a Rat Model of 3,4-Dihydroxyphenyl-L-Alanine-Induced Dyskinesia," The Journal of Neuroscience 26(37):9448-9461, Society for Neuroscience, United States (2006).

(56) References Cited

OTHER PUBLICATIONS

Whitham et al., "Lymphocytes from SJL/J Mice Immunized with Spinal Cord Respond Selectively to a Peptide of Proteolipid Protein and Transfer Relapsing Demyelinating Experimental Autoimmune Encephalomyelitis", The Journal of Immunology, Jan. 1, 1991, pp. 101-107, vol. 146, No. 1.
Whitton, P.S., "Inflammation as a causative factor in the aetiology of Parkinson's disease," British Journal of Pharmacology 150:963-976, Nature Publishing Group, England (2007).
Wilcock, D.M., et aL, "Amyloid reduction by amyloid-b vaccination also reduces mouse tau pathology and protects from neuron loss in two mouse models of Alzheimer's disease," J. Neurosci. 29(25):7957-7965, Society for Neuroscience, United States (2009).
Witte et al., "Monoclonal Antibodies Targeting the VEGF Receptor-2 (Flk1/KDR) as an Anti-Angiogenic Therapeutic Strategy", Cancer and Metastasis Reviews, 1998, pp. 155-161, vol. 17.
Wolburg et al., "The Disturbed Blood-Brain Barrier in Human Glioblastoma", Molecular Aspects of Medicine, 2012, pp. 579-589, vol. 33.
Wu et al., "Humanization of a Murine Monoclonal Antibody by Simultaneous Optimization of Framework and CDR Residues", J. Mol. Biol., 1999, pp. 151-162, vol. 294.
Wu, "Simultaneous Humanization and Affinity Optimization of Monoclonal Antibodies", Methods in Molecular Biology, Jan. 2003, pp. 197-212, vol. 207, Humana Press, Inc., New Jersey, United States.
Xiao-Guang et al., "Preparation and Identification of Monoclonal Antibodies Against CD100 Molecule", Chinese Journal of Cellular and Molecular Immunology, Jan. 2003, pp. 80-82, vol. 19 No. 1, Abstract.
Young et al., "Efficient Isolation of Genes by Using Antibody Probes", Proceedings of the National Academy of Sciences, Mar. 1983, pp. 1194-1196, vol. 80, National Academy of Sciences, United States.
Yu et al., "Interaction Between Bevacizumab and Murine VEGF-A: A Reassessment", Investigative Ophthalmology & Visual Science, Feb. 2008, pp. 522-527, vol. 49 No. 2.
Zhong, Z., et al., "ALS-causing SOD1 mutants generate vascular changes prior to motor neuron degeneration," Nat. Neurosci. 11(4):420-422, Nature Publishing Group, United States (2008).
Zhou et al, "Semaphorin 4D Cooperates with VEGF to Promote Angiogenesis and Tumor Progression", Angiogenesis, 2012, pp. 391-407, vol. 15 Issue 3.
Zhu et al., "Semaphorin 4D (CD100) Is Expressed on the Surface of Human Platelets and Protrolytically Shed During Platelet Activation", Blood, Nov. 2003, Abstract No. 1043, vol. 102 No. 11, The American Society of Hematology, United States (Abstract Only).
Zlokovic, "Neurovascular Pathways to Neurodegeneration in Alzheimer's Disease and other Disorders", Nature Reviews-Neuroscience, Dec. 2011, pp. 723-738, vol. 12.
Zlokovic, B.V., "The Blood-Brain Banicr in Health and Chronic Neurodegenerative Disorders," Neuron 57:178-201, Elsevier Inc., United States (2008).
Fanning et al., "Development of the Immunoglobulin Repertoire", Clinical Immunology and Immunopathology, Apr. 1, 1996, pp. 1-14, vol. 79 No. 1.
Ferrara, N., "VEGF and the quest for tumour angiogenesis factors," Nat. Rev. Cancer 2(10):795-803, Nature Pub. Group, England (2002).
Ferrara, N., et al., "The biology of VEGF and its receptors," Nat. Med. 9(6):669-676, Nature Publishing Company, United States (2003).
Fishwild et al., "High-Avidity Human IgGK Monoclonal Antibodies from a Novel Strain of Minilocus Transgenic Mice", Nature Biotechnology, May 1996, pp. 845-851, vol. 14, Nature Publishing Group, United States.
Fonsatti et al., "Highlights on Endoglin (CD105): From Basic Findings Towards Clinical Application in Human Cancer", Journal of Translational Medicine, 2004, vol. 2:18, 7 pages.

Furuyama et al., "Identification of a Novel Transmembrane Semaphorin Expressed on Lymphocytes", Journal of Biological Chemistry, Dec. 27, 1996, pp. 33376-33381, vol. 271 No. 52.
Galmiche et al., "Expression of a Functional Single Chain Antibody on the Surface of Extracellular Enveloped Vaccinia Virus as a Step Towards Selective Tumour Cell Targeting", Journal of General Virology, 1997, pp. 3019-3027, vol. 78, Great Britain.
Garbuzova-Davis et al., "Amyotrophic Lateral Sclerosis: A Neurovascular Disease", Brain Research, 2011, pp. 113-125, vol. 1398.
Gauld et al., "B Cell Antigen Receptor Signaling: Roles in Cell Development and Disease", Science, May 2002, pp. 1641-1642, vol. 296, The American Association for the Advancement of Science, Untied States.
Gerber, H.P. and Ferrara, N., "Pharmacology and pharmacodynamics of bevacizumab as monotherapy or in combination with cytotoxic therapy in preclinical studies," Cancer Res 65(3):671-680, American Association for Cancer Research, United tates (2005).
Gilden et al., "Varicella Zoster Virus Vasculopathies: Diverse Clinical Manifestations, Laboratory Features, Pathogenesis, and Treatment", The Lancet Neurology, Aug. 2009, pp. 731-740, vol. 8 No. 8.
Giordano et al., "The Semaphorin 4D Receptor Controls Invasive Growth by Coupling with Met", Nature Cell Biology, Sep. 2002, pp. 720-724, vol. 4 No. 9, Nature Publishing Group, England.
Glaser et al., "Dissection of the Combining Site in a Humanized Anti-Tac Antibody", The Journal of Immunology, Oct. 15, 1992, pp. 2607-2614, vol. 149 No. 8.
Goldsby et al., "Autoimmunity", Kuby Immunology, 2000, pp. 502-504, vol. 4, W.H. Freeman and Company, United States.
Goldstein, G.W. and Betz, A.L.., "The Blood-Brain Barrier," Scientific American 255(3):74-83, New York (1986).
Gonzalez-Velasquez, F.J., et al., "Soluble aggregates of the amyloid-b protein selectively stimulate permeability in human brain microvascular endothelial monolayers," J. Neurochem. 107:466-477, International Society for Neurochemistry, England (2008).
Gouttefangeas et al., "Differential Proliferative Responses in Subsets of Human CD28+ Cells Delineated by BB27 mAb", International Immunology, Nov. 1993, pp. 423-430, vol. 6 No. 3, Oxford University Press, Oxford.
Gowdie et al., "Primary and Secondary Central Nervous System Vasculitis", Journal of Child Neurology, 2012, pp. 1448-1459, vol. 27 No. 11.
Grupp et al, "Chimeric Antigen Receptor-Modified T Cells for Acute Lymphoid Leukemia", New England Journal of Medicine, 2013, pp. 1509-1518, vol. 368.
Guido et al., "Virtual Screening and its Integration with Modern Drug Design Technologies", Current Medicinal Chemistry, 2008, pp. 37-46, vol. 15 No. 1, Bentham Science Publishers Ltd.
Gura, "Systems for Identifying New Drugs are Often Faulty", Science, Nov. 7, 1997, pp. 1041-1042, vol. 278, No. 5340.
Gursoy-Ozdemir et al., "Microvascular Protection is Essential for Successful Neuroprotection in Stroke", Journal of Neurochemistry, 2012, pp. 2-11, vol. 123 Suppl. 2.
Hajj-Ali et al., "Primary Angiitis of the Central Nervous System", Autoimmunity Reviews, 2013, pp. 463-466, vol. 12.
Hall et al., "Human CD100, A Novel Leukocyte Semaphorin That Promotes B-Cell Aggregation and Differentiation", Proceeding of the National Academy of Sciences, Oct. 1996, pp. 11780-11785, vol. 93, National Academy of Sciences.
Hawkins, B.T. and Davis, T.P., "The Blood-Brain Barrier/ Neurovascular Unit in Health and Disease," Pharmacological Reviews 57(2):173-185, The American Society for Pharmacology and Experimental Therapeutics, United States (2005).
Hebert et al., "The Molecular Dating Game: An Antibody Heavy Chain Hangs Loose with a Chaperone while Waiting for Its Life Partner", Molecular Cell, 2009, pp. 635-636, vol. 34 No. 6, Cell Press, United States.
Herold et al., "CD100 Defines a Newly Identified 150-kDa Human Lymphocyte Surface Structure" T-Cell Antigens—Papers, 1994, pp. 50-51, vol. T1.

(56) References Cited

OTHER PUBLICATIONS

Hicklin, D.J. and Ellis, L.M., "Role of the vascular endothelial growth factor pathway in tumor growth and angiogenesis," J. Clin. Oncol. 23(5):1011-1027, American Society of Clinical Oncology, United States (2005).
Higgins et al, Enhancing Immune responses to Tumor-associated Antigens, Cancer Biology and Therapy, 2009, pp. 1440-1449, vol. 8 Issue 15.
Hinson et al., "Neurological Autoimmunity Targeting Aquaporin-4", Neuroscience, 2010, pp. 1009-1018, vol. 168.
Ho, Q.T. and Kuo, C.J., "Vascular endothelial growth factor: biology and therapeutic applications," Int. J. Biochem. Cell Biol. 39(7-8):1349-1357, Elsevier, Netherlands (2007).
International Preliminary Report on Patentability (Chapter I) for PCT/US2012/059757 dated Apr. 24, 2014.
International Preliminary Report on Patentability (Chapter I) for PCT/US2013/034133 dated Oct. 9, 2014.
International Preliminary Report on Patentability (Chapter I) for PCT/US2013/040661 dated Nov. 20, 2014.
International Preliminary Report on Patentability for PCT/JP2012/003113 dated Nov. 28, 2013.
International Search Report and Written Opinion for International Application No. PCT/US12/59757, United States Patent Office, United States, dated Dec. 18, 2012.
International Search Report and Written Opinion for PCT/JP2012/003113 dated Jul. 10, 2012.
International Search Report and Written Opinion for PCT/US2010/034116 dated Nov. 8, 2010.
International Search Report and Written Opinion for PCT/US2013/034133 dated Jun. 17, 2013.
International Search Report and Written Opinion for PCT/US2014/043466 dated Nov. 5, 2014.
International Search Report and Written Opinion for PCT/US2014/060129 dated Jan. 15, 2015.
International Search Report and Written Opinion for PCT/US2014/061592 dated Jan. 21, 2015.
Ito et al., "Sema4D/Plexin-B1 Activates GSK-3beta Through R-Ras GAP Activity, Inducing Growth Cone Collapse", EMBO Reports, 2006, pp. 704-709, vol. 7 No. 7.
Iwahashi et al., "CDR Substitutions of a Humanized Monoclonal Antibody (CC49): Contributions of Individual CDRs to Antigen Binding and Immunogenicity", Molecular Immunology, 1999, pp. 1079-1091, vol. 36.
Jain, "Barriers to Drug Delivery in Solid Tumors", Scientific American, Jul. 1994, pp. 58-65, vol. 27 No. 1.
Jain, R.K., "Molecular regulation of vessel maturation," Nat Med. 9(6):685-693, Nature Publishing. Company, United States (2003).
Janssen, B.J., et al., "Structural basis of semaphorin-plexin signaling," Nature 467:1118-1122, Nature Publishing Group, England (2010).
Kalaria, Rajesh N. "The Blood-Brain Barrier and Cerebral Microcirculation in Alzheimer Disease," Cerebrovascular and Brain Metabolism Reviews 4:226-260, Raven Press, Ltd., New York (1992).
Kato et al, "Semaphorin 4D, a lymphocyte semaphorin, Enhances Tumor Cell Motility Through Binding its Receptor, Plexin B1, in Pancreatic Cancer", 2011 Cancer Sci pp. 2029-2037, vol. 102.
Kim, K.J., et al., "Inhibition of vascular endothelial growth factor-induced angiogenesis suppresses tumour growth in vivo," Nature 362(6423):841-844, Nature Publishing Group, England (1993).
Southwell et al., "Anti-semaphorin 4D Immunotherapy Ameliorates Neuropathology and Some Cognitive Impairment in the YAC128 Mouse Model of Huntington Disease", Neurobiology of Disease, pp. 46-56, vol. 76 (2015).
Fisher et al., "Development of Anti-SEMA4D Monoclonal Antibody for the Treatment of Multiple Sclerosis", 5th Joint Triennial Congress of the European and Americas Committees for Treatment and Research in Multiple Sclerosis, Oct. 19, 2011-Oct. 22, 2011, Amsterdam, The Netherlands, retrieved from http://registration.akm.ch/einsicht.php?XNABSTRACT_ID=138346&XNSPRACCHE on Jun. 10, 2015, Abstract.

Cornelius et al., "Abstract 936: Nonclinical Safety and Pharmacology of VX15/2503: a Humanized IgG4 Monoclonal Antibody to SEMA4D", Cancer Research, Apr. 15, 2012, retrieved from http://cancerres,aacrjournals.org/content/72/8_Supplement/936.short on Sep. 25, 2015, the whole document, Abstract.
Del Zoppo et al., Expansion of the Time Window for Treatment of Acute Ischemic Stroke With Intravenous Tissue Plasminogen Activator: A Science Advisory From the American Heart Association /American Stroke Association, Stroke, Journal of the American Heart Association, vol. 40, pp. 2945-2948 (2009).
Basile et al., J Biol. Chem. 282(48): 34888-34895 (2007).
Baxter et al., Nat. Rev. Immunol., 2(6):439-446, 2002.
Bretscher et al., Science, 169(3950):1042-1049, 1970.
Callahan et al., J. Leukoc. Biol., 94(1):41-53, 2013.
Drake et al., Adv. Immunol., 90:51-81, 2006.
Fong et al., "Potentiating Endogenous Antitumor Immunity to Prostate Cancer through Combination Immunotherapy with CTLA4 Blockade and GM-CSF", Cancer Research, Jan. 15, 2009, pp. 609-615, vol. 69, Issue 2.
Genova et al., Expert Opin. Biol. Ther., 12(7):939-948, 2012.
Grosso et al., Cancer Imm., 13:5-14, 2013.
Intlekofer et al., J. Leukoc. Biol., 94(1):25-39, 2013.
Jenkins et al., J. Exp. Med., 165(2):302-319, 1987.
Jonason et al., "Development of an anti-SEMA4D monoclonial antibody for the treatment of Multiple Sclerosis", 5th Joint Triennial Congress of the European and Americas Committees for Treatment and Research in Multiple Sclerosis, Oct. 19-22, 2011, Amsterdam, The Netherlands.
Kanai et al., "Anti-Tumor and Anti-Metastatic Effects of Human-Vascular-Endothelial-Growth-Factor-Neutralizing Antibody on Human Colon and Gastric Carcinoma Xenotransplanted Orthotopically into Nude Mice", International Journal of Cancer, 1998, pp. 933-936, vol. 77.
Lafferty et al., Aust. J. Exp. Biol. Med. Sci., 53(1):27-42, 1975.
McDermott et al., Cancer Med., 2(5):662-673, 2013.
Office Action for U.S. Appl. No. 13/649,651 dated Jul. 28, 2015.
Office Action for U.S. Appl. No. 13/797,048 dated Jun. 17, 2015.
Okuno et al., "The Role of Immune Semaphorins in Multiple Sclerosis", Federation of European Biochemical Societies Letters, 2011, pp. 3829-3835, vol. 585.
Peranzoni et al., Cell. Mol. Life Sci., 70:4431-4448, 2013.
Royal et al., J. Immunother., 33(8):828-833, 2010.
Slovin et al., Ann. Oncol., 24(7):1813-1821, 2013.
Sprinzl et al., J. Hepatol., 59(1):9-10, 2013.
Steinman, Lawrence, "Multiple Sclerosis: A Two-Stage Disease", Nature Immunology, 2001, 2(9): 762-764.
Topalian et al., N. Engl. J. Med., 366(26):2443-2454, 2012.
Yang et al., J. Immunother., 30(8)825-830, 2007.
Zhang et al., "Sema 4D/CD100-plexin B is a Multifunctional Counter-Receptor", Cellular and Molecular Immunology, 2013, pp. 97-98, vol. 10.
Dickinson, B.J., "Molecular Mechanisms of Axon Guide," Science, 2002, pp. 1959-1964, vol. 298, No. 5600.
Huber et al., "Signaling At the Growth Cone: Ligand-Receptor Complexes and the Control of Axon Growth and Guidance," Annual Review Neuroscience, 2003, pp. 509-563, vol. 26.
Basile et al., "Class IV semaphorins promote angiogenesis by stimulating Rho-initiated pathways through plexin-B," Cancer Research, 2004, pp. 5212-5224, vol. 64.
Svendsen et al., Long-Term Survival of Human Central Nervous System Progenitor Cells Transplanted into a Rat Model of Parkinson's Disease, Exp. Neurol. 148(1): 135-146 (1997).
Palmer et al., "Progenitor Cells from Human Brain After Death", Nature, vol. 411, No. 6833, pp. 42-43 (2001).
Palmer et al., "The Adult Rat Hippocampus Contains Primordial Neural Stem Cells", Molecular Cell Neurosci , vol. 8, No. 6, pp. 389-404 (1997).
Lutgens et al., "Requirement for CD154 in the Progression of Atherosclerosis", Nat. Med., 1999, pp. 1313-1316, vol. 11.
Mach et al., "Activation of Monocyte/Macrophage Functions Related to Acute Atheroma Complication by Ligation of CD40", Circulation, 1997, pp. 396-399, vol. 96.

(56) References Cited

OTHER PUBLICATIONS

Shisabuddin, "The Search for Neural Progenitor Cells: Prospects for the Therapy of Neurodegenerative Disease", Molecular Medicine Today 5(1):474-480 (1999).

Witherden et al., The CD100 Receptor Interacts with Its Plexin B2 Ligand to Regulate Epidermal γσ Cell Function, Immunity 37(2):314-325 (2012).

Fabis et al., "Loss of Blood-Brain Barrier Integrity in the Spinal Cord is Common to Experimental Allergic Encephalomyelitis in Knockout Mouse Models," Proceedings of the National Academy of Sciences of the United States of America, pp. 5656-5661, vol. 104, No. 13, Mar. 27, 2007.

Okuno et al., "Examination of Effect of Sema4D Inhibitition Therapy Against Experimental Autoimmune Encephalomyelitis (EAE) and its Action Mechanism," Department of Immunopathology, Research Institute for Microbial Diseases and Department of Neurology, Osaka University Graduate, School of Medicine, pp. 1094, vol. 50, No. 12 (2010).

Maragakis et al., "Mechanisms of Disease: Astrocytes in Neurodegenerative Disease," Nature Clinical Practice Neurology, pp. 679-698, vol. 2, No. 12 (2006).

Brambilla et al., "Astrocyte Signaling and Neurodegeneration, New Insights into CNS Disorders," Prion, pp. 29-36, vol. 7, No. 1, Jan. 2013.

Vargas et al., "Astrogliosis in Amyotrophic Lateral Sclerosis: ROle and Therapeutic Potential of Astrocytes," Neurotherapeutics, pp. 471-481, vol. 7, No. 4 (2010).

Evans et al., "Inflammation and Neurovascular Changes in Amyotrophic Lateral Sclerosis," Molecular and Cellular Neuroscience, pp. 34-41, No. 53 (2013).

Anthony et al., "Special Issue Commentary: The Changing Face of Inflammation in the Brain," Molecular and Cellular Neuroscience, pp. 1-5, No. 53 (2013).

Okuno et al., "Roles of Sema4D_Plexin-B1 Interactions in the Central Nervouse System for Pathogenesis of Experimental Autoimmune Encephalomy Elitis," The Joumal of Immunology, pp. 1499-1506, vol. 184, No. 3 (2009).

Vezzani et al., "The Role of Inflammation in Epilepsy," Nature Reviews Neurology, pp. 31-40, vol. 7 No. 1, Jan. 2011.

Ulm, Notice of Allowance and Notice of Allowability issued in U.S. Appl. No. 14/519,965, 5 pages, dated Nov. 9, 2016.

Yamaguchi et al., "Sema4D as an Inhibitory Regulator in Oligodendrocyte Development", Molecular and Cellular Neuroscience, Dec. 14, 2011, pp. 290-299, vol. 49.

\* cited by examiner

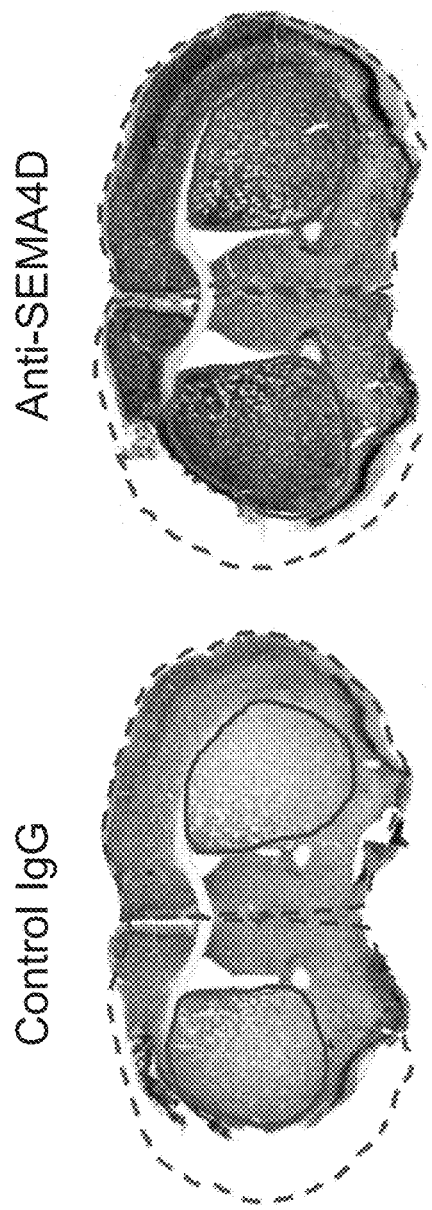
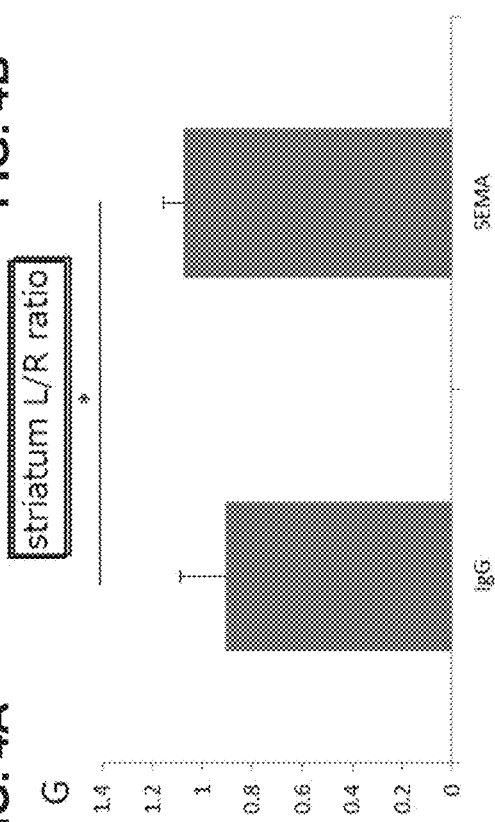

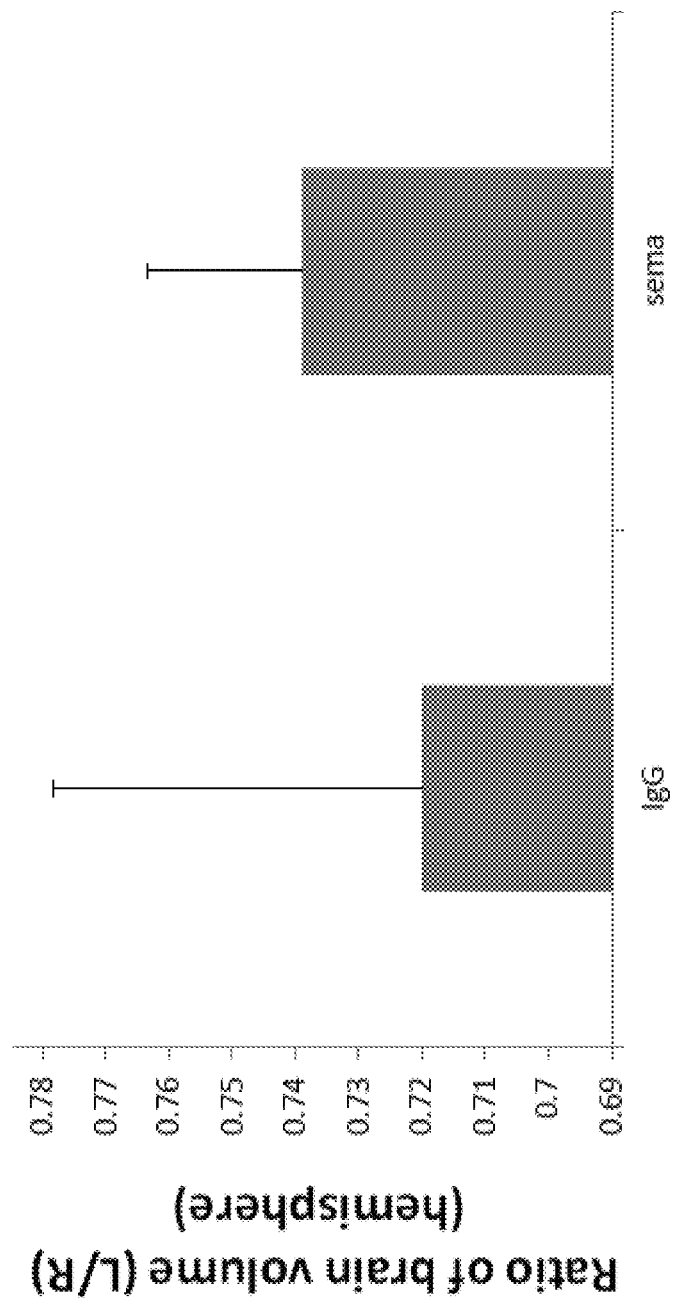

USE OF SEMAPHORIN-4D BINDING MOLECULES TO PROMOTE NEUROGENESIS FOLLOWING STROKE

CROSS-REFERENCE TO RELATED APPLICATIONS

This application claims priority benefit to U.S. Provisional Appl. No. 61/646,119, filed on May 11, 2012, the content of which is hereby incorporated by reference in its entirety.

REFERENCE TO SEQUENCE LISTING SUBMITTED ELECTRONICALLY

The content of the electronically submitted sequence listing in ASCII text file (Name: "18430720001_Sequence-Listing.txt"; Size: 7,519 bytes; and Date of Creation: Mar. 14, 2013) filed herewith is incorporated herein by reference in its entirety.

BACKGROUND OF THE INVENTION

Semaphorin 4D (SEMA4D), also known as CD100, is a transmembrane protein that belongs to the semaphorin gene family. SEMA4D is expressed on the cell surface as a homodimer, but upon cell activation SEMA4D can be released from the cell surface via proteolytic cleavage to generate sSEMA4D, a soluble form of the protein, which is also biologically active. See Suzuki et al., Nature Rev. Immunol. 3:159-167 (2003); Kikutani et al., Nature Immunol. 9:17-23 (2008).

SEMA4D is expressed at high levels in lymphoid organs, including the spleen, thymus, and lymph nodes, and in non-lymphoid organs, such as the brain, heart, and kidney. In lymphoid organs, SEMA4D is abundantly expressed on resting T cells but only weakly expressed on resting B cells and antigen-presenting cells (APCs), such as dendritic cells (DCs). Its expression, however, is upregulated in these cells following activation by various stimuli. The release of soluble SEMA4D from immune cells is also increased by cell activation.

SEMA4D has been implicated in the development of autoimmune demyelinating diseases such as multiple sclerosis and certain cancers. The failure of the mammalian nervous system to completely regenerate after injury is a major clinical problem. Neural damage as a result of stroke or trauma to the brain, as well as neurodegenerative diseases such as Alzheimer's disease, are a leading cause of death and disability. While the role of SEMA4D signaling through its receptors, e.g., Plexin-B1, on angiogenesis is well-recognized, the effect of SEMA4D signaling on promoting neurogenesis remains unclear. There remains, therefore, a need to provide a solution to the unmet medical need for therapeutic means of neuroregeneration.

BRIEF SUMMARY OF THE INVENTION

Methods for using Semaphorin-4D binding molecules for promotion of neurogenesis are disclosed herein. Evidence is presented demonstrating that SEMA4D can compromise the ability of neural cells to regenerate. According to aspects of the invention illustrated herein, there is provided a method for promoting neurogenesis in neural tissue of a patient exhibiting at least one symptom of a central nervous system disorder, the method comprising administering to a subject in need thereof an effective amount of an isolated binding molecule which specifically binds to and/or inhibits semaphorin-4D (SEMA4D).

According to aspects of the invention illustrated herein, there is provided a method for increasing the number of progenitor cells in a subject with a disorder of the central nervous system comprising administering to the subject an effective amount of an isolated binding molecule which specifically binds to semaphorin-4D (SEMA4D), wherein the binding to SEMA4D acts to increase the number of progenitor cells.

According to aspects of the invention illustrated herein, there is provided a method for promoting neurogenesis in neural tissue of a patient exhibiting at least one symptom of a central nervous system disorder, comprising administering to a subject an effective amount of an isolated binding molecule which specifically binds to SEMA4D, wherein the binding molecule competitively inhibits a reference monoclonal antibody selected from the group consisting of VX15/2503 or 67 from specifically binding to SEMA4D.

According to aspects of the invention illustrated herein, there is provided a method for alleviating a symptom of a disease or disorder of the central nervous system, such as stroke, in a patient comprising administering to the subject an effective amount of an isolated binding molecule which specifically binds to and/or inhibits semaphorin-4D (SEMA4D), wherein the binding to SEMA4D acts to alleviate the symptom.

BRIEF DESCRIPTION OF THE DRAWINGS/FIGURES

FIG. 1: Schematic of experimental protocol for middle cerebral artery (MCA) occlusion described in the Examples.

FIGS. 2A-2E: Show neural stem/precursor cells in brain samples stained for Nestin/Sox2 in the areas indicated in 2E following occlusion of the middle cerebral artery (MCAO) and treatment with either isotype control ("Control IgG", 2A and 2C) or MAb 67-2 ("Anti-Sema4D-Ab", 2B and 2D). The brain samples were prepared 7 days after MCAO.

FIGS. 3A-3D: Show (A) mRNA expression by RT-PCR with quantitative analysis for (B) Sox2, (C) nestin, and (D) PLP relative to actin control in brain tissue of MCAO mice treated with isotype control ("Control IgG") or MAb 67-2 ("Anti-SEMA4D"). Brain tissue was isolated 7 days after MCAO. Nestin and Sox2 are markers of neural stem precursor cells. PLP is a marker of myelination.

FIGS. 4A-4D: Show relative total volume of brain and striatum in treated and untreated hemispheres in MCAO mice treated with isotype control or MAb 67-2. Measurements were taken 30 days after MCAO. FIGS. 4A-4B show brain sections stained with NeuN from (A) 1 representative isotype control ("Control IgG") mouse and (B) 1 representative anti-SEMA4D antibody-treated ("Anti-SEMA4D") mouse. Brain volume is represented by the volume of the striatum (solid line) and the hemisphere (dotted line). FIGS. 4C-4D show the calculated ratio (L/R) of striatum and hemispheric volume, respectively, for isotype control ("IgG") mouse and anti-SEMA4D antibody-treated ("SEMA") mouse.

FIGS. 5A-5B: Show expression of the mature neuronal cell marker, NeuN, in MCAO mice (A) MAb 67-2 ("Sema4D-Ab") or (B) isotype control ("Control IgG") at 30 days after MCAO. The striatum at the border of cerebral infarction is indicated with arrows.

Figure 6:
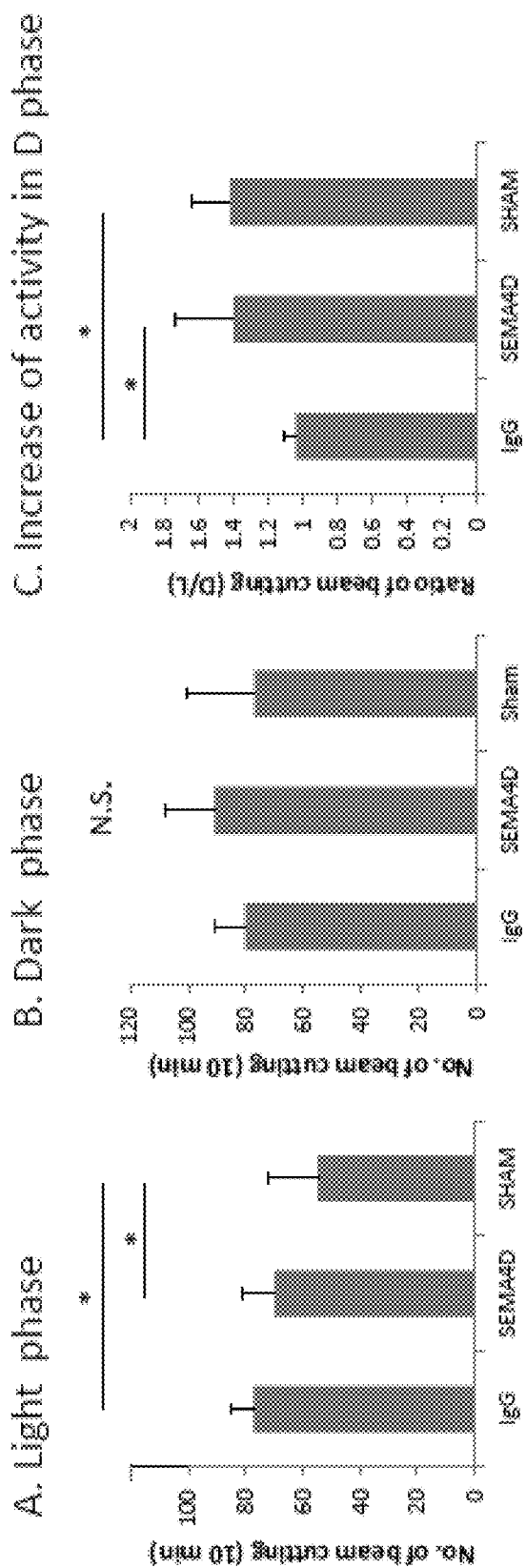

FIGS. 6A-C: Shows light and dark phase open-field locomotor activity of mice following MCAO and treatment with isotype control ("IgG") or MAb 67-2 ("SEMA4D") at 30 days after MCAO, or mice treated with sham surgery ("SHAM"). FIGS. 6A-6B show locomotor activity in light phase and dark phase, respectively. FIG. 6C shows that the ratio of dark/light phase (D/L) in locomotion activity.

Figure 7:
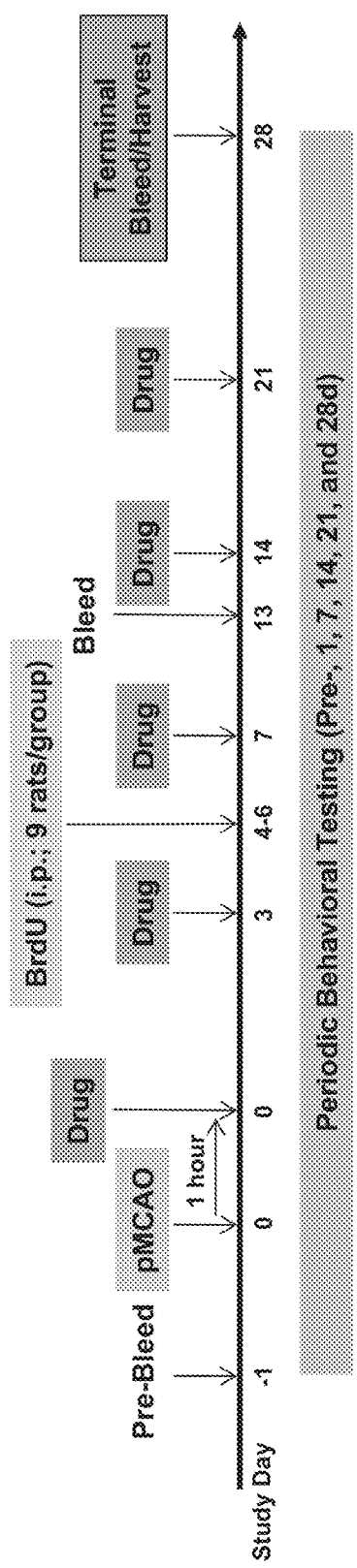

FIG. 7: Shows a schematic of the experimental protocol described in Example 6.

DETAILED DESCRIPTION OF THE INVENTION

I. Definitions

It is to be noted that the term "a" or "an" entity refers to one or more of that entity; for example, "an anti-SEMA4D antibody" is understood to represent one or more anti-SEMA4D antibodies. As such, the terms "a" (or "an"), "one or more," and "at least one" can be used interchangeably herein.

The phrase "neurogenesis" is defined herein as proliferation, differentiation, migration and/or survival of a neural cell in vivo or in vitro. In various embodiments, the neural cell is an adult, fetal, or embryonic neural stem cell or population of cells. The cells may be located in the central nervous system or elsewhere in an animal or human being. The cells may also be in a tissue, such as neural tissue. In some embodiments, the neural cell is an adult, fetal, or embryonic progenitor cell or population of cells, or a population of cells comprising a mixture of stem cells and progenitor cells. Neural cells include all brain stem cells, all brain progenitor cells, and all brain precursor cells. Neurogenesis includes neurogenesis as it occurs during normal development, as well as neural regeneration that occurs following disease, damage or therapeutic intervention, such as by the treatment described herein.

The term "neural cell", "stem cell", "neural stem cell", "precursor cell", "neural stem/precursor cells" (NSPC) or "neural stem/progenitor cells" (NSPC) are used interchangeably to refer to an undifferentiated cell that is capable of self-renewal and differentiation into neurons, astrocytes, and/or oligodendrocytes.

The term "progenitor cell" (e.g., neural progenitor cell), as used herein, refers to a cell derived from a stem cell that is not itself a stem cell. Some progenitor cells can produce progeny that are capable of differentiating into more than one cell type. Neural progenitor cells include neuronal progenitor cells, which produce neurons, and glial progenitor cells that produce astroglial and/or oligodendroglial cells.

As used herein, the term "central nervous system disorder" or a "CNS disorder" refers to a neurodegenerative disorder, acute brain injury (e.g. stroke, head injury, cerebral palsy, cerebral infarction, spinal cord injury, traumatic injury) and certain central nervous system "CNS" dysfunctions (e.g. depression, epilepsy, and schizophrenia).

As used herein, the term "neurodegenerative disorder" refers to Alzheimer's disease, Huntington's Disease, Amyotrophic Lateral Sclerosis, Parkinson's Disease, and multiple sclerosis. It should be noted that a CNS disorder may also be a neuroinflammatory disorder. It should be appreciated that a neurodegenerative disorder may include neuroinflammation. However, it is possible for a neurodegenerative disorder to exist in the absence of obvious neuroinflammation. This is the case, for example, in late stage secondary progressive multiple sclerosis.

As used herein, the term "acute brain injury" refers to stroke, head injury, cerebral palsy, cerebral infarction, spinal cord injury, and traumatic injury.

As used herein, the term "CNS dysfunctions" refers to depression, epilepsy, and schizophrenia.

The term "therapeutically effective amount" refers to an amount of an antibody, polypeptide, polynucleotide, small organic molecule, or other drug effective to "treat" a disease or disorder in a subject or mammal. In the case of a neuroinflammatory disorder, the therapeutically effective amount of the drug can promote neurogenesis by increasing, for instance, the proliferation, differentiation, migration and/or survival of neural stem/precursor cells; reduce, retard or stop a decrease in neural cells; inhibit, e.g., suppress, retard, prevent, stop, or reverse a reduction in neural cells; increase the number, density and/or concentration of neural cells; change in the morphology or function of neural cells; or a change in the interactions among neural cells; relieve to some extent one or more of the symptoms associated with a reduction in neural cells, e.g., neuroinflammatory disorders; reduce morbidity and mortality; improve quality of life; or a combination of such effects.

Terms such as "treating" or "treatment" or "to treat" or "alleviating" or "to alleviate" refer to both 1) therapeutic measures that cure, slow down, lessen symptoms of, reverse, and/or halt progression of a diagnosed pathologic condition or disorder and 2) prophylactic or preventative measures that prevent and/or slow the development of a targeted pathologic condition or disorder. Thus those in need of treatment include those already with the disorder; those prone to have the disorder; and those in whom the disorder is to be prevented. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

By "subject" or "individual" or "animal" or "patient" or "mammal," is meant any subject, particularly a mammalian subject, for whom diagnosis, prognosis, or therapy is desired. Mammalian subjects include humans, domestic animals, farm animals, and zoo, sports, or pet animals such as dogs, cats, guinea pigs, rabbits, rats, mice, horses, cattle, cows, bears, and so on.

As used herein, phrases such as "a subject that would benefit from administration of an anti-SEMA4D antibody" and "an animal in need of treatment" includes subjects, such as mammalian subjects, that would benefit from administration of an anti-SEMA4D antibody or other SEMA4D binding molecule used, e.g., for detection of a SEMA4D polypeptide (e.g., for a diagnostic procedure) and/or from treatment, i.e., palliation or prevention of a disease, with an anti-SEMA4D antibody or other SEMA4D binding molecule.

A "binding molecule" or "antigen binding molecule" of the present invention refers in its broadest sense to a molecule that specifically binds an antigenic determinant. In one embodiment, the binding molecule specifically binds to SEMA4D, e.g., to a transmembrane SEMA4D polypeptide of about 150 kDa or a soluble SEMA4D polypeptide of about 120 kDa (commonly referred to as sSEMA4D). In another embodiment, a binding molecule of the invention is an antibody or an antigen binding fragment thereof. In another embodiment, a binding molecule of the invention comprises at least one heavy or light chain CDR of an antibody molecule. In another embodiment, a binding molecule of the invention comprises at least two CDRs from one or more antibody molecules. In another embodiment, a binding molecule of the invention comprises at least three CDRs from one or more antibody molecules. In another embodiment, a binding molecule of the invention comprises at least four CDRs from one or more antibody molecules. In another embodiment, a binding molecule of the invention comprises at least five CDRs from one or more antibody molecules. In another embodiment, a binding molecule of the invention comprises at least six CDRs from one or more antibody molecules.

The present invention is directed to a method of promoting neurogenesis in a subject having neurodegenerative disorders, neuroinflammatory disorders, acute brain injuries, and certain CNS dysfunctions comprising administering to the subject an anti-SEMA4D binding molecule, e.g., an antibody, or antigen-binding fragment, variant, or derivative thereof. Unless specifically referring to full-sized antibodies such as naturally occurring antibodies, the term "anti-SEMA4D antibody" encompasses full-sized antibodies as well as antigen-binding fragments, variants, analogs, or derivatives of such antibodies, e.g., naturally occurring antibody or immunoglobulin molecules or engineered antibody molecules or fragments that bind antigen in a manner similar to antibody molecules.

As used herein, "human" or "fully human" antibodies include antibodies having the amino acid sequence of a human immunoglobulin and include antibodies isolated from human immunoglobulin libraries or from animals transgenic for one or more human immunoglobulins and that do not express endogenous immunoglobulins, as described infra and, for example, in U.S. Pat. No. 5,939,598 by Kucherlapati et al. "Human" or "fully human" antibodies also include antibodies comprising at least the variable domain of a heavy chain, or at least the variable domains of a heavy chain and a light chain, where the variable domain(s) have the amino acid sequence of human immunoglobulin variable domain(s).

"Human" or "fully human" antibodies also include "human" or "fully human" antibodies, as described above, that comprise, consist essentially of, or consist of, variants (including derivatives) of antibody molecules (e.g., the VH regions and/or VL regions) described herein, which antibodies or fragments thereof immunospecifically bind to a SEMA4D polypeptide or fragment or variant thereof. Standard techniques known to those of skill in the art can be used to introduce mutations in the nucleotide sequence encoding a human anti-SEMA4D antibody, including, but not limited to, site-directed mutagenesis and PCR-mediated mutagenesis which result in amino acid substitutions. Preferably, the variants (including derivatives) encode less than 50 amino acid substitutions, less than 40 amino acid substitutions, less than 30 amino acid substitutions, less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the reference VH region, VHCDR1, VHCDR2, VHCDR3, VL region, VLCDR1, VLCDR2, or VLCDR3.

In certain embodiments, the amino acid substitutions are conservative amino acid substitution, discussed further below. Alternatively, mutations can be introduced randomly along all or part of the coding sequence, such as by saturation mutagenesis, and the resultant mutants can be screened for biological activity to identify mutants that retain activity (e.g., the ability to bind a SEMA4D polypeptide, e.g., human, murine, or both human and murine SEMA4D). Such variants (or derivatives thereof) of "human" or "fully human" antibodies can also be referred to as human or fully human antibodies that are "optimized" or "optimized for antigen binding" and include antibodies that have improved affinity to antigen.

The terms "antibody" and "immunoglobulin" are used interchangeably herein. An antibody or immunoglobulin comprises at least the variable domain of a heavy chain, and normally comprises at least the variable domains of a heavy chain and a light chain. Basic immunoglobulin structures in vertebrate systems are relatively well understood. See, e.g., Harlow et al. (1988) Antibodies: A Laboratory Manual (2nd ed.; Cold Spring Harbor Laboratory Press).

As used herein, the term "immunoglobulin" comprises various broad classes of polypeptides that can be distinguished biochemically. Those skilled in the art will appreciate that heavy chains are classified as gamma, mu, alpha, delta, or epsilon, ($\gamma$, $\mu$, $\alpha$, $\delta$, $\epsilon$) with some subclasses among them (e.g., $\gamma 1$-$\gamma 4$). It is the nature of this chain that determines the "class" of the antibody as IgG, IgM, IgA IgG, or IgE, respectively. The immunoglobulin subclasses (isotypes) e.g., IgG1, IgG2, IgG3, IgG4, IgA1, etc. are well characterized and are known to confer functional specialization. Modified versions of each of these classes and isotypes are readily discernable to the skilled artisan in view of the instant disclosure and, accordingly, are within the scope of the instant invention. All immunoglobulin classes are clearly within the scope of the present invention, the following discussion will generally be directed to the IgG class of immunoglobulin molecules. With regard to IgG, a standard immunoglobulin molecule comprises two identical light chain polypeptides of molecular weight approximately 23,000 Daltons, and two identical heavy chain polypeptides of molecular weight 53,000-70,000. The four chains are typically joined by disulfide bonds in a "Y" configuration wherein the light chains bracket the heavy chains starting at the mouth of the "Y" and continuing through the variable region.

Light chains are classified as either kappa or lambda ($\kappa$, $\lambda$). Each heavy chain class may be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain.

Both the light and heavy chains are divided into regions of structural and functional homology. The terms "constant" and "variable" are used functionally. In this regard, it will be appreciated that the variable domains of both the light (VL or VK) and heavy (VH) chain portions determine antigen recognition and specificity. Conversely, the constant domains of the light chain (CL) and the heavy chain (CH1, CH2 or CH3) confer important biological properties such as secretion, transplacental mobility, Fc receptor binding, complement binding, and the like. By convention the numbering of the constant region domains increases as they become more distal from the antigen binding site or aminoterminus of the antibody. The N-terminal portion is a variable region and at the C-terminal portion is a constant region; the CH3 and CL domains actually comprise the carboxy-terminus of the heavy and light chain, respectively.

As indicated above, the variable region allows the antibody to selectively recognize and specifically bind epitopes on antigens. That is, the VL domain and VH domain, or subset of the complementarity determining regions (CDRs) within these variable domains, of an antibody combine to form the variable region that defines a three dimensional antigen binding site. This quaternary antibody structure forms the antigen binding site present at the end of each arm of the Y. More specifically, the antigen binding site is defined by three CDRs on each of the VH and VL chains. In some instances, e.g., certain immunoglobulin molecules derived from camelid species or engineered based on camelid immunoglobulins, a complete immunoglobulin molecule may consist of heavy chains only, with no light chains. See, e.g., Hamers-Casterman et al., *Nature* 363:446-448 (1993).

In naturally occurring antibodies, the six "complementarity determining regions" or "CDRs" present in each antigen binding domain are short, non-contiguous sequences of amino acids that are specifically positioned to form the antigen binding domain as the antibody assumes its three dimensional configuration in an aqueous environment. The remainder of the amino acids in the antigen binding domains, referred to as "framework" regions, show less inter-molecular variability. The framework regions largely adopt a β-sheet conformation and the CDRs form loops that connect, and in some cases form part of, the β-sheet structure. Thus, framework regions act to form a scaffold that provides for positioning the CDRs in correct orientation by inter-chain, non-covalent interactions. The antigen binding domain formed by the positioned CDRs defines a surface complementary to the epitope on the immunoreactive antigen. This complementary surface promotes the non-covalent binding of the antibody to its cognate epitope. The amino acids comprising the CDRs and the framework regions, respectively, can be readily identified for any given heavy or light chain variable domain by one of ordinary skill in the art, since they have been precisely defined (see below).

In the case where there are two or more definitions of a term that is used and/or accepted within the art, the definition of the term as used herein is intended to include all such meanings unless explicitly stated to the contrary. A specific example is the use of the term "complementarity determining region" ("CDR") to describe the non-contiguous antigen combining sites found within the variable region of both heavy and light chain polypeptides. This particular region has been described by Kabat et al. (1983) U.S. Dept. of Health and Human Services, "Sequences of Proteins of Immunological Interest" and by Chothia and Lesk, *J. Mol. Biol.* 196:901-917 (1987), which are incorporated herein by reference, where the definitions include overlapping or subsets of amino acid residues when compared against each other. Nevertheless, application of either definition to refer to a CDR of an antibody or variants thereof is intended to be within the scope of the term as defined and used herein. The appropriate amino acid residues that encompass the CDRs as defined by each of the above cited references are set forth below in Table 1 as a comparison. The exact residue numbers that encompass a particular CDR will vary depending on the sequence and size of the CDR. Those skilled in the art can routinely determine which residues comprise a particular CDR given the variable region amino acid sequence of the antibody.

TABLE 1

CDR Definitions[1]

|  | Kabat | Chothia |
| --- | --- | --- |
| VH CDR1 | 31-35 | 26-32 |
| VH CDR2 | 50-65 | 52-58 |
| VH CDR3 | 95-102 | 95-102 |
| VL CDR1 | 24-34 | 26-32 |
| VL CDR2 | 50-56 | 50-52 |
| VL CDR3 | 89-97 | 91-96 |

[1]Numbering of all CDR definitions in Table 1 is according to the numbering conventions set forth by Kabat et al. (see below).

Kabat et al. also defined a numbering system for variable domain sequences that is applicable to any antibody. One of ordinary skill in the art can unambiguously assign this system of "Kabat numbering" to any variable domain sequence, without reliance on any experimental data beyond the sequence itself. As used herein, "Kabat numbering" refers to the numbering system set forth by Kabat et al. (1983) U.S. Dept. of Health and Human Services, "Sequence of Proteins of Immunological Interest." Unless otherwise specified, references to the numbering of specific amino acid residue positions in an anti-SEMA4D antibody or antigen-binding fragment, variant, or derivative thereof of the present invention are according to the Kabat numbering system.

Antibodies or antigen-binding fragments, variants, or derivatives thereof of the invention include, but are not limited to, polyclonal, monoclonal, multispecific, human, humanized, primatized, or chimeric antibodies, single-chain antibodies, epitope-binding fragments, e.g., Fab, Fab' and F(ab')$_2$, Fd, Fvs, single-chain Fvs (scFv), disulfide-linked Fvs (sdFv), fragments comprising either a VL or VH domain, fragments produced by a Fab expression library, and anti-idiotypic (anti-Id) antibodies (including, e.g., anti-Id antibodies to anti-SEMA4D antibodies disclosed herein). ScFv molecules are known in the art and are described, e.g., in U.S. Pat. No. 5,892,019. Immunoglobulin or antibody molecules of the invention can be of any type (e.g., IgG, IgE, IgM, IgD, IgA, and IgY), class (e.g., IgG1, IgG2, IgG3, IgG4, IgA1, and IgA2, etc.), or subclass of immunoglobulin molecule.

As used herein, the term "heavy chain portion" includes amino acid sequences derived from an immunoglobulin heavy chain. In certain embodiments, a polypeptide comprising a heavy chain portion comprises at least one of: a VH domain, a CH1 domain, a hinge (e.g., upper, middle, and/or lower hinge region) domain, a CH2 domain, a CH3 domain, or a variant or fragment thereof. For example, a binding polypeptide for use in the invention may comprise a polypeptide chain comprising a CH1 domain; a polypeptide chain comprising a CH1 domain, at least a portion of a hinge domain, and a CH2 domain; a polypeptide chain comprising a CH1 domain and a CH3 domain; a polypeptide chain comprising a CH1 domain, at least a portion of a hinge domain, and a CH3 domain, or a polypeptide chain comprising a CH1 domain, at least a portion of a hinge domain, a CH2 domain, and a CH3 domain. In another embodiment, a polypeptide of the invention comprises a polypeptide chain comprising a CH3 domain. Further, a binding polypeptide for use in the invention may lack at least a portion of a CH2 domain (e.g., all or part of a CH2 domain). As set forth above, it will be understood by one of ordinary skill in the art that these domains (e.g., the heavy chain portions) may be modified such that they vary in amino acid sequence from the naturally occurring immunoglobulin molecule.

In certain anti-SEMA4D antibodies, or antigen-binding fragments, variants, or derivatives thereof disclosed herein, the heavy chain portions of one polypeptide chain of a multimer are identical to those on a second polypeptide chain of the multimer. Alternatively, heavy chain portion-containing monomers of the invention are not identical. For example, each monomer may comprise a different target binding site, forming, for example, a bispecific antibody.

The heavy chain portions of a binding molecule for use in the methods disclosed herein may be derived from different immunoglobulin molecules. For example, a heavy chain portion of a polypeptide can comprise a $C_{H1}$ domain derived from an IgG1 molecule and a hinge region derived from an IgG3 molecule. In another example, a heavy chain portion can comprise a hinge region derived, in part, from an IgG1 molecule and, in part, from an IgG3 molecule. In another example, a heavy chain portion can comprise a chimeric hinge derived, in part, from an IgG1 molecule and, in part, from an IgG4 molecule.

As used herein, the term "light chain portion" includes amino acid sequences derived from an immunoglobulin light chain, e.g., a kappa or lambda light chain. Preferably, the light chain portion comprises at least one of a VL or CL domain.

Anti-SEMA4D antibodies, or antigen-binding fragments, variants, or derivatives thereof disclosed herein may be described or specified in terms of the epitope(s) or portion(s) of an antigen, e.g., a target polypeptide disclosed herein (e.g., SEMA4D) that they recognize or specifically bind. The portion of a target polypeptide that specifically interacts with the antigen binding domain of an antibody is an "epitope," or an "antigenic determinant." A target polypeptide can comprise a single epitope, but typically comprises at least two epitopes, and can include any number of epitopes, depending on the size, conformation, and type of antigen. Furthermore, it should be noted that an "epitope" on a target polypeptide may be or may include non-polypeptide elements, e.g., an epitope may include a carbohydrate side chain.

The minimum size of a peptide or polypeptide epitope for an antibody is thought to be about four to five amino acids. Peptide or polypeptide epitopes preferably contain at least seven, more preferably at least nine and most preferably between at least about 15 to about 30 amino acids. Since a CDR can recognize an antigenic peptide or polypeptide in its tertiary form, the amino acids comprising an epitope need not be contiguous, and in some cases, may not even be on the same peptide chain. A peptide or polypeptide epitope recognized by anti-SEMA4D antibodies of the present invention may contain a sequence of at least 4, at least 5, at least 6, at least 7, more preferably at least 8, at least 9, at least 10, at least 15, at least 20, at least 25, or between about 15 to about 30 contiguous or non-contiguous amino acids of SEMA4D.

By "specifically binds," it is generally meant that an antibody binds to an epitope via its antigen binding domain, and that the binding entails some complementarity between the antigen binding domain and the epitope. According to this definition, an antibody is said to "specifically bind" to an epitope when it binds to that epitope, via its antigen binding domain more readily than it would bind to a random, unrelated epitope. The term "specificity" is used herein to qualify the relative affinity by which a certain antibody binds to a certain epitope. For example, antibody "A" may be deemed to have a higher specificity for a given epitope than antibody "B," or antibody "A" may be said to bind to epitope "C" with a higher specificity than it has for related epitope "D."

By "preferentially binds," it is meant that the antibody specifically binds to an epitope more readily than it would bind to a related, similar, homologous, or analogous epitope. Thus, an antibody that "preferentially binds" to a given epitope would more likely bind to that epitope than to a related epitope, even though such an antibody may cross-react with the related epitope.

By way of non-limiting example, an antibody may be considered to bind a first epitope preferentially if it binds said first epitope with a dissociation constant ($K_D$) that is less than the antibody's $K_D$ for the second epitope. In another non-limiting example, an antibody may be considered to bind a first antigen preferentially if it binds the first epitope with an affinity that is at least one order of magnitude less than the antibody's $K_D$ for the second epitope. In another non-limiting example, an antibody may be considered to bind a first epitope preferentially if it binds the first epitope with an affinity that is at least two orders of magnitude less than the antibody's $K_D$ for the second epitope.

In another non-limiting example, an antibody may be considered to bind a first epitope preferentially if it binds the first epitope with an off rate (k(off)) that is less than the antibody's k(off) for the second epitope. In another non-limiting example, an antibody may be considered to bind a first epitope preferentially if it binds the first epitope with an affinity that is at least one order of magnitude less than the antibody's k(off) for the second epitope. In another non-limiting example, an antibody may be considered to bind a first epitope preferentially if it binds the first epitope with an affinity that is at least two orders of magnitude less than the antibody's k(off) for the second epitope. An antibody or or antigen-binding fragment, variant, or derivative disclosed herein may be said to bind a target polypeptide disclosed herein (e.g., SEMA4D, e.g., human, murine, or both human and murine SEMA4D) or a fragment or variant thereof with an off rate (k(off)) of less than or equal to $5 \times 10^{-2}$ sec$^{-1}$, $10^{-2}$ sec$^{-1}$, $5 \times 10^{-3}$ sec$^{-1}$ or $10^{-3}$ sec$^{-1}$. More preferably, an antibody of the invention may be said to bind a target polypeptide disclosed herein (e.g., SEMA4D, e.g., human, murine, or both human and murine SEMA4D) or a fragment or variant thereof with an off rate (k(off)) less than or equal to $5 \times 10^{-4}$ sec$^{-1}$, $10^{-4}$ sec$^{-1}$, $5 \times 10^{-5}$ sec$^{-1}$, or $10^{-5}$ sec$^{-1}$, $5 \times 10^{-6}$ sec$^{-1}$, $10^{-6}$ sec$^{-1}$, $5 \times 10^{-7}$ sec$^{-1}$ or $10^{-7}$ sec$^{-1}$.

An antibody or antigen-binding fragment, variant, or derivative disclosed herein may be said to bind a target polypeptide disclosed herein (e.g., SEMA4D, e.g., human, murine, or both human and murine SEMA4D) or a fragment or variant thereof with an on rate (k(on)) of greater than or equal to $10^3$ M$^{-1}$ sec$^{-1}$, $5 \times 10^3$ M$^{-1}$ sec$^{-1}$, $10^4$ M$^{-1}$ sec$^{-1}$ or $5 \times 10^4$ M$^{-1}$ sec$^{-1}$. More preferably, an antibody of the invention may be said to bind a target polypeptide disclosed herein (e.g., SEMA4D, e.g., human, murine, or both human and murine SEMA4D) or a fragment or variant thereof with an on rate (k(on)) greater than or equal to $10^5$ M$^{-1}$ sec$^{-1}$, $5 \times 10^5$ M$^{-1}$ sec$^{-1}$, $10^6$ M$^{-1}$ sec$^{-1}$, or $5 \times 10^6$ M$^{-1}$ sec$^{-1}$ or $10^7$ M$^{-1}$ sec$^{-1}$.

An antibody is said to competitively inhibit binding of a reference antibody to a given epitope if it preferentially binds to that epitope to the extent that it blocks, to some degree, binding of the reference antibody to the epitope. Competitive inhibition may be determined by any method known in the art, for example, competition ELISA assays. An antibody may be said to competitively inhibit binding of the reference antibody to a given epitope by at least 90%, at least 80%, at least 70%, at least 60%, or at least 50%.

As used herein, the term "affinity" refers to a measure of the strength of the binding of an individual epitope with the CDR of an immunoglobulin molecule. See, e.g., Harlow et al. (1988) Antibodies: A Laboratory Manual (Cold Spring Harbor Laboratory Press, 2nd ed.) pages 27-28. As used herein, the term "avidity" refers to the overall stability of the complex between a population of immunoglobulins and an antigen, that is, the functional combining strength of an immunoglobulin mixture with the antigen. See, e.g., Harlow at pages 29-34. Avidity is related to both the affinity of individual immunoglobulin molecules in the population with specific epitopes, and also the valencies of the immunoglobulins and the antigen. For example, the interaction between a bivalent monoclonal antibody and an antigen with a highly repeating epitope structure, such as a polymer, would be one of high avidity.

Anti-SEMA4D antibodies or antigen-binding fragments, variants, or derivatives thereof of the invention may also be described or specified in terms of their cross-reactivity. As used herein, the term "cross-reactivity" refers to the ability of an antibody, specific for one antigen, to react with a second antigen; a measure of relatedness between two different antigenic substances. Thus, an antibody is cross reactive if it binds to an epitope other than the one that induced its formation. The cross reactive epitope generally contains many of the same complementary structural features as the inducing epitope, and in some cases, may actually fit better than the original.

For example, certain antibodies have some degree of cross-reactivity, in that they bind related, but non-identical epitopes, e.g., epitopes with at least 95%, at least 90%, at least 85%, at least 80%, at least 75%, at least 70%, at least 65%, at least 60%, at least 55%, and at least 50% identity (as calculated using methods known in the art and described herein) to a reference epitope. An antibody may be said to have little or no cross-reactivity if it does not bind epitopes with less than 95%, less than 90%, less than 85%, less than 80%, less than 75%, less than 70%, less than 65%, less than 60%, less than 55%, and less than 50% identity (as calculated using methods known in the art and described herein) to a reference epitope. An antibody may be deemed "highly specific" for a certain epitope, if it does not bind any other analog, ortholog, or homolog of that epitope.

Anti-SEMA4D binding molecules, e.g., antibodies or antigen-binding fragments, variants or derivatives thereof, of the invention may also be described or specified in terms of their binding affinity to a polypeptide of the invention, e.g., SEMA4D, e.g., human, murine, or both human and murine SEMA4D. Preferred binding affinities include those with a dissociation constant or Kd less than $5 \times 10^{-2}$ M, $10^{-2}$ M, $5 \times 10^{-3}$ M, $10^{-3}$ M, $5 \times 10^{-4}$ M, $10^{-4}$M, $5 \times 10^{-5}$M, $10^{-5}$M, $5 \times 10^{-6}$M, $10^{-6}$M, $5 \times 10^{-7}$ M, $10^{-7}$ M, $5 \times 10^{-8}$M, $10^{-8}$M, $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M, or $10^{-15}$ M. In certain embodiments, the anti-SEMA4D binding molecule, e.g., an antibody or antigen binding fragment thereof, of the invention binds human SEMA4D with a Kd of about $5 \times 10^{-9}$ to about $6 \times 10^{-9}$. In another embodiment, the anti-SEMA4D binding molecule, e.g., an antibody or antigen binding fragment thereof, of the invention binds murine SEMA4D with a Kd of about $1 \times 10^{-9}$ to about $2 \times 10^{-9}$.

As used herein, the term "chimeric antibody" will be held to mean any antibody wherein the immunoreactive region or site is obtained or derived from a first species and the constant region (which may be intact, partial or modified in accordance with the instant invention) is obtained from a second species. In preferred embodiments the target binding region or site will be from a non-human source (e.g., mouse or primate) and the constant region is human.

As used herein, the term "engineered antibody" refers to an antibody in which the variable domain in either the heavy or light chain or both is altered by at least partial replacement of one or more CDRs from an antibody of known specificity and, if necessary, by partial framework region replacement and sequence changing. Although the CDRs may be derived from an antibody of the same class or even subclass as the antibody from which the framework regions are derived, it is envisaged that the CDRs will be derived from an antibody of different class and preferably from an antibody from a different species. An engineered antibody in which one or more "donor" CDRs from a non-human antibody of known specificity is grafted into a human heavy or light chain framework region is referred to herein as a "humanized antibody." It may not be necessary to replace all of the CDRs with the complete CDRs from the donor variable domain to transfer the antigen binding capacity of one variable domain to another. Rather, it may only be necessary to transfer those residues that are necessary to maintain the activity of the target binding site.

It is further recognized that the framework regions within the variable domain in a heavy or light chain, or both, of a humanized antibody may comprise solely residues of human origin, in which case these framework regions of the humanized antibody are referred to as "fully human framework regions" (for example, MAb VX15/2503, disclosed in U.S. Patent Appl. Publication No. US 2010/0285036 A1 as MAb 2503, incorporated herein by reference in its entirety). Alternatively, one or more residues of the framework region(s) of the donor variable domain can be engineered within the corresponding position of the human framework region(s) of a variable domain in a heavy or light chain, or both, of a humanized antibody if necessary to maintain proper binding or to enhance binding to the SEMA4D antigen. A human framework region that has been engineered in this manner would thus comprise a mixture of human and donor framework residues, and is referred to herein as a "partially human framework region."

For example, humanization of an anti-SEMA4D antibody can be essentially performed following the method of Winter and co-workers (Jones et al., Nature 321:522-525 (1986); Riechmann et al., Nature 332:323-327 (1988); Verhoeyen et al., Science 239:1534-1536 (1988)), by substituting rodent or mutant rodent CDRs or CDR sequences for the corresponding sequences of a human anti-SEMA4D antibody. See also U.S. Pat. Nos. 5,225,539; 5,585,089; 5,693,761; 5,693,762; 5,859,205; herein incorporated by reference. The resulting humanized anti-SEMA4D antibody would comprise at least one rodent or mutant rodent CDR within the fully human framework regions of the variable domain of the heavy and/or light chain of the humanized antibody. In some instances, residues within the framework regions of one or more variable domains of the humanized anti-SEMA4D antibody are replaced by corresponding non-human (for example, rodent) residues (see, for example, U.S. Pat. Nos. 5,585,089; 5,693,761; 5,693,762; and 6,180, 370), in which case the resulting humanized anti-SEMA4D antibody would comprise partially human framework regions within the variable domain of the heavy and/or light chain.

Furthermore, humanized antibodies can comprise residues that are not found in the recipient antibody or in the donor antibody. These modifications are made to further refine antibody performance (e.g., to obtain desired affinity). In general, the humanized antibody will comprise substantially all of at least one, and typically two, variable domains, in which all or substantially all of the CDRs correspond to those of a non-human immunoglobulin and all or substantially all of the framework regions are those of a human immunoglobulin sequence. The humanized antibody optionally also will comprise at least a portion of an immunoglobulin constant region (Fc), typically that of a human immunoglobulin. For further details see Jones et al., *Nature* 331:522-525 (1986); Riechmann et al., *Nature* 332:323-329 (1988); and Presta, *Curr. Op. Struct. Biol.* 2:593-596 (1992); herein incorporated by reference. Accordingly, such "humanized" antibodies may include antibodies wherein substantially less than an intact human variable domain has been substituted by the corresponding sequence from a non-human species. In practice, humanized antibodies are typically human antibodies in which some CDR residues and possibly some framework residues are substituted by residues from analogous sites in rodent antibodies. See, for example, U.S. Pat. Nos. 5,225,539; 5,585,089; 5,693,761; 5,693,762; 5,859,205. See also U.S. Pat. No. 6,180,370, and International Publication No. WO 01/27160, where humanized antibodies and techniques for producing humanized antibodies having improved affinity for a predetermined antigen are disclosed.

II. Neural Stem/Precursor Cells or Neural Stem/Progenitor Cells (NSPCs)

Neurogenesis refers generally to the production of new neurons. Traditionally, neurogenesis was thought to occur only during the embryonic and early postnatal periods and to have no significant role in the adult brain. In recent years, however, neurogenesis has been postulated to occur in selected regions of adult mammalian brain and may be stimulated in these as well as other regions in response to injury.

During development of the central nervous system and peripheral nervous system, neural stem cells proliferate and divide into progenitor cells that eventually differentiate into cell types that compose the adult brain. Cells derived from the neural tube give rise to neurons and glia of the CNS, while cells derived from the neural crest give rise to the cells of the peripheral nervous system (PNS).

Neural stem/progenitor cells and their therapeutic use have been described in the art, for example, see U.S. Pat. No. 6,638,501, Bjornson et al.; U.S. Pat. No. 6,541,255, Snyder et al.; U.S. Pat. No. 6,498,018, Carpenter; U.S. Patent Application 20020012903, Goldman et al.; Palmer et al. (2001) Nature 411(6833):42-3; Palmer et al. (1997) Mol Cell Neurosci. 8(6):389-404; Svendsen et al. (1997) Exp. Neurol. 148(1):135-46 and Shihabuddin (1999) Mol Med Today. 5(11):474-80. Methods for isolation and culture of neural stem cells are also known in the art, see U.S. Pat. Nos. 6,777,233; 6,497,872, and US Patent application 20030143737A1. All these references are specifically incorporated by reference.

Neural stem and precursor cells participate in normal development through migration along well-established migratory pathways to disseminated CNS regions, differentiation into cell types in response to microenvironmental cues, and interspersion with host progenitors and their progeny. Human neural stem cells are capable of expressing foreign transgenes in vivo in these disseminated locations. As such, these cells have the potential to be used to treat a variety of conditions affecting the CNS, including degenerative disorders (e.g. Alzheimer's and Parkinson's), acute brain injury (e.g. stroke, head injury, cerebral palsy) and a large number of CNS dysfunctions (e.g. depression, epilepsy, and schizophrenia).

In recent years neurodegenerative disease has become an important concern due to the expanding elderly population which is at greatest risk for these disorders. These diseases, which include Alzheimer's Disease, Huntington's Disease, Amyotrophic Lateral Sclerosis, and Parkinson's Disease, have been linked to the degeneration of neural cells in particular locations of the CNS, leading to the inability of these cells or the brain region to carry out their intended function.

Degeneration in a brain region known as the basal ganglia can lead to diseases with various cognitive and motor symptoms, depending on the exact location. The basal ganglia consists of many separate regions, including the striatum (which consists of the caudate and putamen), the globus pallidus, the substantia nigra, substantia innominate, ventral palladium, nucleus basalis of Meynert, ventral tegmental area and the subthalamic nucleus.

In Alzheimer's disease, for instance, there is cellular degeneration of the forebrain and cerebral cortex. In addition, there appears to be localized degeneration in an area of the basal ganglia, the nucleus basalis of Meynert. This nucleus normally sends cholinergic projections to the cerebral cortex which are thought to participate in cognitive functions including memory. In Huntington's Chorea, on the other hand, there is degeneration of neurons in the striatum, which leads to involuntary jerking movements in the host. In Parkinson's disease, furthermore, degeneration is seen in another area of the basal ganglia, the substantia nigra par compacta. This area normally sends dopaminergic connections to the dorsal striatum which are important in regulating movement. Therapy for Parkinson's disease has centered upon restoring dopaminergic activity to this circuit. Degeneration of other regions of the basal ganglia is also possible. For example, degeneration of a small region called the subthalamic nucleus is associated with violent flinging movements of the extremities in a condition called ballismus, while degeneration in the putamen and globus pallidus is associated with a condition of slow writhing movements or athetosis.

In addition to neurodegenerative diseases, acute brain injuries often result in the loss of neural cells, inappropriate functioning of the affected brain region, and subsequent behavior abnormalities. In addition to cell loss, an individual may suffer from an abnormal functioning of existing neural cells. This may be due to inappropriate firing of neurons, or the abnormal synthesis, release, and processing of neurotransmitters. These dysfunctions may be the result of well-studied and characterized disorders such as depression and epilepsy, or less understood disorders such as neurosis and psychosis. Other forms of neurological impairment can occur as a result of neural degeneration, such as amyotrophic lateral sclerosis and cerebral palsy, or as a result of more acute CNS trauma, such as that which occurs in traumatic brain injury (TBI) and stroke.

III. Target Polypeptide Description

As used herein, the terms "semaphorin-4D," "SEMA4D" and "SEMA4D polypeptide" are used interchangeably, as are "SEMA4D" and "Sema4D." In certain embodiments, SEMA4D is expressed on the surface of or secreted by a cell. In another embodiment, SEMA4D is membrane bound. In another embodiments, SEMA4D is soluble, e.g., sSEMA4D. In other embodiments, SEMA4D may include a full-sized SEMA4D or a fragment thereof, or a SEMA4D variant polypeptide, wherein the fragment of SEMA4D or SEMA4D variant polypeptide retains some or all functional properties of the full-sized SEMA4D.

The full-sized human SEMA4D protein is a homodimeric transmembrane protein consisting of two polypeptide chains of 150 kDa. SEMA4D belongs to the semaphorin family of cell surface receptors and is also referred to as CD100. Both human and mouse SEMA4D/Sema4D are proteolytically cleaved from their transmembrane form to generate 120-kDa soluble forms, indicating the existence of two Sema4D isoforms (Kumanogoh et al., *J. Cell Science* 116(7):3464 (2003)). Semaphorins consist of soluble and membrane-bound proteins that were originally defined as axonal-guidance factors during development which play an important role in establishing precise connections between neurons and their appropriate target. Structurally considered a class IV semaphorin, SEMA4D consists of an amino-terminal signal sequence followed by a characteristic 'Sema' domain, which contains 17 conserved cysteine residues, an Ig-like domain, a lysine-rich stretch, a hydrophobic transmembrane region, and a cytoplasmic tail.

Each polypeptide chain of SEMA4D includes a signal sequence of about 13 amino acids followed by a semaphorin domain of about 512 amino acids, an immunoglobulin-like (Ig-like) domain of about 65 amino acids, a lysine-rich stretch of 104 amino acids, a hydrophobic transmembrane region of about 19 amino acids, and a cytoplasmic tail of 110 amino acids. A consensus site for tyrosine phosphorylation in the cytoplasmic tail supports the predicted association of SEMA4D with a tyrosine kinase (Schlossman, et al., Eds. (1995) Leucocyte Typing V (Oxford University Press, Oxford).

SEMA4D is known to have at least three receptors: Plexin-B1, Plexin-B2, and CD72. One of the receptors, Plexin-B1, is expressed in non-lymphoid tissues and has been shown to be a high affinity (1 nM) receptor for SEMA4D (Tamagnone et al., *Cell* 99:71-80 (1999)). In certain embodiments the endothelial cells express Plexin-B1. SEMA4D stimulation of Plexin-B1 signaling has been shown to induce growth cone collapse of neurons, and to induce process extension collapse and apoptosis of oligo-dendrocytes (Giraudon et al., *J. Immunol.* 172:1246-1255 (2004); Giraudon et al., *NeuroMolecular Med.* 7:207-216 (2005)). After binding to SEMA4D, Plexin-B1 signaling mediates the inactivation of R-Ras, leading to a decrease in the integrin mediated attachment to the extracellular matrix, and can also result in activation of RhoA, leading to cell collapse by reorganization of the cytoskeleton. See Kruger et al., *Nature Rev. Mol. Cell Biol.* 6:789-800 (2005); Pasterkamp, *TRENDS in Cell Biology* 15:61-64 (2005)). Plexin-B2 has an intermediate affinity for SEMA4D and a recent report indicates that PLXNB2 is expressed on keratinocytes and activates SEMA4D-positive γδ T cells to contribute to epithelial repair (Witherden et al., *Immunity.* 2012 Aug. 24; 37(2):314-25).

In lymphoid tissues CD72 is utilized as a low affinity (300 nM) SEMA4D receptor (Kumanogoh et al., *Immunity* 13:621-631 (2000)). B cells and APCs express CD72, and anti-CD72 antibodies have many of the same effects as sSEMA4D, such as enhancement of CD40-induced B cell responses and B cell shedding of CD23. CD72 is thought to act as a negative regulator of B cell responses by recruiting the tyrosine phosphatase SHP-1, which can associate with many inhibitory receptors. Interaction of SEMA4D with CD72 results in the dissociation of SHP-1, and the loss of this negative activation signal. SEMA4D has been shown to promote T cell stimulation and B cell aggregation and survival in vitro. The addition of SEMA4D-expressing cells or sSEMA4D enhances CD40-induced B cell proliferation and immunoglobulin production in vitro, and accelerates in vivo antibody responses (Ishida et al., *Inter. Immunol.* 15:1027-1034 (2003); Kumanogoh and H. Kukutani, *Trends in Immunol.* 22:670-676 (2001)). sSEMA4D enhances the CD40 induced maturation of DCs, including up-regulation of costimulatory molecules and increased secretion of IL-12. In addition, sSEMA4D can inhibit immune cell migration, which can be reversed by addition of blocking anti-SEMA4D antibodies (Elhabazi et al., *J. Immunol.* 166:4341-4347 (2001); Delaire et al., *J. Immunol.* 166:4348-4354 (2001)).

Sema4D is expressed at high levels in lymphoid organs, including the spleen, thymus, and lymph nodes, and in non-lymphoid organs, such as the brain, heart, and kidney. In lymphoid organs, Sema4D is abundantly expressed on resting T cells but only weakly expressed on resting B cells and antigen-presenting cells (APCs), such as dendritic cells (DCs). Cellular activation increases the surface expression of SEMA4D as well as the generation of soluble SEMA4D (sSEMA4D).

The expression pattern of SEMA4D suggests that it plays an important physiological as well as pathological role in the immune system. SEMA4D has been shown to promote B cell activation, aggregation and survival; enhance CD40-induced proliferation and antibody production; enhance antibody response to T cell dependent antigens; increase T cell proliferation; enhance dendritic cell maturation and ability to stimulate T cells; and is directly implicated in demyelination and axonal degeneration (Shi et al., *Immunity* 13:633-642 (2000); Kumanogoh et al., *J Immunol* 169:1175-1181 (2002); and Watanabe et al., *J Immunol* 167:4321-4328 (2001)).

SEMA4D knock out (SEMA4D−/−) mice have provided additional evidence that SEMA4D plays an important role in both humoral and cellular immune responses. There are no known abnormalities of non-lymphoid tissues in SEMA4D−/− mice. Dendritic cells (DCs) from the SEMA4D−/− mice have poor allostimulatory ability and show defects in expression of costimulatory molecules, which can be rescued by the addition of sSEMA4D. Mice deficient in SEMA4D (SEMA4D−/−) fail to develop experimental autoimmune encephalomyelitis induced by myelin oligodendrocyte glycoprotein peptide, because myelin oligodendrocyte glycoprotein-specific T cells are poorly generated in the absence of SEMA4D (Kumanogoh et al., *J Immunol* 169:1175-1181 (2002)). A significant amount of soluble SEMA4D is also detected in the sera of autoimmunity-prone MRL/lpr mice (model of systemic autoimmune diseases such as SLE), but not in normal mice. Further, the levels of sSEMA4D correlate with levels of auto-antibodies and increase with age (Wang et al., *Blood* 97:3498-3504 (2001)). Soluble SEMA4D has also been shown to accumulate in the cerebral spinal fluid and sera of patients with demyelinating disease, and sSEMA4D induces apoptosis of human pluripotent neural precursors (Dev cells), and both inhibits process extension and induces apoptosis of rat oligodendrocytes in vitro (Giraudon et al., *J Immunol* 172 (2):1246-1255 (2004)). This apoptosis was blocked by an anti-SEMA4D MAb.

IV. Anti-SEMA4D Antibodies

Antibodies that bind SEMA4D have been described in the art. See, for example, US Publ. Nos. 2008/0219971 A1, US 2010/0285036 A1, and US 2006/0233793 A1, International Patent Applications WO 93/14125, WO 2008/100995, and WO 2010/129917, and Herold et al., *Int. Immunol.* 7(1): 1-8 (1995), each of which is herein incorporated in its entirety by reference.

The invention generally relates to a method of promoting neurogenesis in a subject having neurodegenerative disorders, neuroinflammatory disorders, acute brain injuries, and certain CNS dysfunctions e.g., a human patient, comprising administration of an antibody which specifically binds to SEMA4D, or an antigen-binding fragment, variant, or derivative thereof. In certain embodiments, the antibody blocks the interaction of SEMA4D with one or more of its receptors, e.g., Plexin-B1. Anti-SEMA4D antibodies having these properties can be used in the methods provided herein. Antibodies that can be used include, but are not limited to MAbs VX15/2503, 67, and 76 and antigen-binding fragments, variants, or derivatives thereof which are fully described in US 2010/0285036 A1. Additional antibodies which can be used in the methods provided herein include the BD16 and BB18 antibodies described in US 2006/0233793 A1 as well as antigen-binding fragments, variants, or derivatives thereof; or any of MAb 301, MAb 1893, MAb 657, MAb 1807, MAb 1656, MAb 1808, Mab 59, MAb 2191, MAb 2274, MAb 2275, MAb 2276, MAb 2277, MAb 2278, MAb 2279, MAb 2280, MAb 2281, MAb 2282, MAb 2283, MAb 2284, and MAb 2285, as well as any fragments, variants or derivatives thereof as described in US 2008/0219971 A1. In certain embodiments an anti-SEMA4D antibody for use in the methods provided herein binds human, murine, or both human and murine SEMA4D. Also useful are antibodies which bind to the same epitope as any of the aforementioned antibodies and/or antibodies which competitively inhibit any of the aforementioned antibodies.

The amino acid sequences of the MAb 67 VH and VK genes are shown below with the CDR1, CDR2 and CDR3 regions underlined.

```
MAb 67 VH:
                                             (SEQ ID NO: 1)
QVQLQQSGPELVKPGASVKISCKASGYSFSDYYMHWVKQSPENSLEWIG

QINPTTGGASYNQKFKGKATLTVDKSSSTAYMQLKSLTSEESAVYYCTR

YYYGRHFDVWGQGTTVTVSS

MAb 67 VK:
                                             (SEQ ID NO: 2)
DIVMTQSPASLAVSLGQRATISCKASQSVDYDGDSYMNWYQQKPGQPPK

LLIYAASNLESGIPARFSGSGSGTDFTLNIHPVEEEDAATYYCQQSNED

PYTFGGGTKLEIK
```

The amino acid sequences of the humanized MAb 67 VH (H2160) and VK (L553) ("MAb VX15/2503") are shown below with the CDR1, CDR2 and CDR3 regions underlined.

```
Sequence of H2160:
                                             (SEQ ID NO: 3)
QVQLVQSGAEVKKPGSSVKVSCKASGYSFSDYYMHWVRQAPGQGLEWMG

QINPTTGGASYNQKFKGKATITVDKSTSTAYMELSSLRSEDTAVYYCAR

YYYGRHFDVWGQGTTVTVSS

Sequence of L553:
                                             (SEQ ID NO: 4)
DIVMTQSPDSLAVSLGERATINCKASQSVDYDGDSYMNWYQQKPGQPPK

LLIYAASNLESGVPDRFSGSGSGTDFTLTISSLQAEDVAVYYCQQSNED

PYTFGQGTKLEIK
```

In certain embodiments, an anti-SEMA4D antibody or antigen-binding fragment, variant, or derivative thereof useful in the methods provided herein has an amino acid sequence that has at least about 80%, about 85%, about 88%, about 89%, about 90%, about 91%, about 92%, about 93%, about 94%, or about 95% sequence identity to the amino acid sequence for a reference anti-SEMA4D antibody molecule, for example VX15/2503 and 67 described above. In a further embodiment, the binding molecule shares at least about 96%, about 97%, about 98%, about 99%, or 100% sequence identity to a reference antibody.

In another embodiment, an anti-SEMA4D antibody or antigen-binding fragment, variant, or derivative thereof useful in the methods provided herein comprises, consists essentially of, or consists of an immunoglobulin heavy chain variable domain (VH domain), where at least one of the CDRs of the VH domain has an amino acid sequence that is at least about 80%, about 85%, about 90%, about 95%, about 96%, about 97%, about 98%, about 99%, or identical to CDR1, CDR2 or CDR3 of SEQ ID NO: 1 or 3.

In another embodiment, an anti-SEMA4D antibody or antigen-binding fragment, variant, or derivative thereof useful in the methods provided herein comprises, consists essentially of, or consists of an immunoglobulin heavy chain variable domain (VH domain), where at least one of the CDRs of the VH domain has an amino acid sequence that is at least about 80%, about 85%, about 90%, about 95%, about 96%, about 97%, about 98%, about 99%, or identical to SEQ ID NO: 5, SEQ ID NO: 6, or SEQ ID NO: 7.

In another embodiment, an anti-SEMA4D antibody or antigen-binding fragment, variant, or derivative thereof useful in the methods provided herein comprises, consists essentially of, or consists of an immunoglobulin heavy chain variable domain (VH domain), where at least one of the CDRs of the VH domain has an amino acid sequence identical, except for 1, 2, 3, 4, or 5 conservative amino acid substitutions, to SEQ ID NO: 5, SEQ ID NO: 6, or SEQ ID NO: 7.

In another embodiment, an anti-SEMA4D antibody or antigen-binding fragment, variant, or derivative thereof useful in the methods provided herein comprises, consists essentially of, or consists of a VH domain that has an amino acid sequence that is at least about 80%, about 85%, about 90%, about 91%, about 92%, about 93%, about 94%, about 95%, about 96%, about 97%, about 98%, about 99%, or 100% identical to SEQ ID NO: 1 or SEQ ID NO: 3, wherein an anti-SEMA4D antibody comprising the encoded VH domain specifically or preferentially binds to SEMA4D.

In another embodiment, an anti-SEMA4D antibody or antigen-binding fragment, variant, or derivative thereof useful in the methods provided herein comprises, consists essentially of, or consists of an immunoglobulin light chain variable domain (VL domain), where at least one of the CDRs of the VL domain has an amino acid sequence that is at least about 80%, about 85%, about 90%, about 95%, about 96%, about 97%, about 98%, about 99%, or identical to CDR1, CDR2 or CDR3 of SEQ ID NO: 2 or 4.

In another embodiment, an anti-SEMA4D antibody or antigen-binding fragment, variant, or derivative thereof useful in the methods provided herein comprises, consists essentially of, or consists of an immunoglobulin light chain variable domain (VL domain), where at least one of the CDRs of the VL domain has an amino acid sequence that is at least about 80%, about 85%, about 90%, about 95%, about 96%, about 97%, about 98%, about 99%, or identical to SEQ ID NO: 8, SEQ ID NO: 9, or SEQ ID NO: 10.

In another embodiment, an anti-SEMA4D antibody or antigen-binding fragment, variant, or derivative thereof useful in the methods provided herein comprises, consists essentially of, or consists of an immunoglobulin light chain variable domain (VL domain), where at least one of the CDRs of the VL domain has an amino acid sequence identical, except for 1, 2, 3, 4, or 5 conservative amino acid substitutions, to SEQ ID NO: 8, SEQ ID NO: 9, or SEQ ID NO: 10.

In a further embodiment, an anti-SEMA4D antibody or antigen-binding fragment, variant, or derivative thereof useful in the methods provided herein comprises, consists essentially of, or consists of a VL domain that has an amino acid sequence that is at least about 80%, about 85%, about 90%, about 91%, about 92%, about 93%, about 94%, about 95%, about 96%, about 97%, about 98%, about 99%, or 100% identical to SEQ ID NO: 2 or SEQ ID NO: 4, wherein an anti-SEMA4D antibody comprising the encoded VL domain specifically or preferentially binds to SEMA4D.

Also included for use in the methods provided herein are polypeptides encoding anti-SEMA4D antibodies, or antigen-binding fragments, variants, or derivatives thereof as described herein, polynucleotides encoding such polypeptides, vectors comprising such polynucleotides, and host cells comprising such vectors or polynucleotides, all for producing anti-SEMA4D antibodies, or antigen-binding fragments, variants, or derivatives thereof for use in the methods described herein.

Suitable biologically active variants of the anti-SEMA4D antibodies of the invention can be used in the methods of the present invention. Such variants will retain the desired binding properties of the parent anti-SEMA4D antibody. Methods for making antibody variants are generally available in the art.

Methods for mutagenesis and nucleotide sequence alterations are well known in the art. See, for example, Walker and Gaastra, eds. (1983) Techniques in Molecular Biology (MacMillan Publishing Company, New York); Kunkel, *Proc. Natl. Acad. Sci. USA* 82:488-492 (1985); Kunkel et al., *Methods Enzymol.* 154:367-382 (1987); Sambrook et al. (1989) Molecular Cloning: A Laboratory Manual (Cold Spring Harbor, N.Y.); U.S. Pat. No. 4,873,192; and the references cited therein; herein incorporated by reference. Guidance as to appropriate amino acid substitutions that do not affect biological activity of the polypeptide of interest may be found in the model of Dayhoff et al. (1978) in Atlas of Protein Sequence and Structure (Natl. Biomed. Res. Found., Washington, D.C.), pp. 345-352, herein incorporated by reference in its entirety. The model of Dayhoff et al. uses the Point Accepted Mutation (PAM) amino acid similarity matrix (PAM 250 matrix) to determine suitable conservative amino acid substitutions. Conservative substitutions, such as exchanging one amino acid with another having similar properties, may be preferred. Examples of conservative amino acid substitutions as taught by the PAM 250 matrix of the Dayhoff et al. model include, but are not limited to, Gly↔Ala, Val↔Ile↔Leu, Asp↔Glu, Lys↔Arg, Asn↔Gln, and Phe↔Trp↔Tyr.

In constructing variants of the anti-SEMA4D binding molecule, e.g., an antibody or antigen-binding fragment thereof, polypeptides of interest, modifications are made such that variants continue to possess the desired properties, e.g., being capable of specifically binding to a SEMA4D, e.g., human, murine, or both human and murine SEMA4D, e.g., expressed on the surface of or secreted by a cell and having SEMA4D blocking activity, as described herein. Obviously, any mutations made in the DNA encoding the variant polypeptide must not place the sequence out of reading frame and preferably will not create complementary regions that could produce secondary mRNA structure. See EP Patent Application Publication No. 75,444.

Methods for measuring anti-SEMA4D binding molecule, e.g., an antibody or antigen-binding fragment, variant, or derivative thereof, binding specificity include, but are not limited to, standard competitive binding assays, assays for monitoring immunoglobulin secretion by T cells or B cells, T cell proliferation assays, apoptosis assays, ELISA assays, and the like. See, for example, such assays disclosed in WO 93/14125; Shi et al., *Immunity* 13:633-642 (2000); Kumanogoh et al., *J Immunol* 169:1175-1181 (2002); Watanabe et al., *J Immunol* 167:4321-4328 (2001); Wang et al., *Blood* 97:3498-3504 (2001); and Giraudon et al., *J Immunol* 172(2):1246-1255 (2004), all of which are herein incorporated by reference.

When the issue is discussed herein whether any particular polypeptide, including the constant regions, CDRs, VH domains, or VL domains disclosed herein, is at least about 65%, about 70%, about 75%, about 80%, about 85%, about 90%, about 91%, about 92%, about 93%, about 94%, about 95%, about 96%, about 97%, about 98%, about 99%, or even about 100% identical to another polypeptide, the % identity can be determined using methods and computer programs/software known in the art such as, but not limited to, the BESTFIT program (Wisconsin Sequence Analysis Package, Version 8 for Unix, Genetics Computer Group, University Research Park, 575 Science Drive, Madison, Wis. 53711). BESTFIT uses the local homology algorithm of Smith and Waterman (1981) Adv. Appl. Math. 2:482-489, to find the best segment of homology between two sequences. When using BESTFIT or any other sequence alignment program to determine whether a particular sequence is, for example, 95% identical to a reference sequence according to the present invention, the parameters are set, of course, such that the percentage of identity is calculated over the full length of the reference polypeptide sequence and that gaps in homology of up to 5% of the total number of amino acids in the reference sequence are allowed.

For purposes of the present invention, percent sequence identity may be determined using the Smith-Waterman homology search algorithm using an affine gap search with a gap open penalty of 12 and a gap extension penalty of 2, BLOSUM matrix of 62. The Smith-Waterman homology search algorithm is taught in Smith and Waterman (1981) Adv. Appl. Math. 2:482-489. A variant may, for example, differ from a reference anti-SEMA4D antibody (e.g., MAb VX15/2503, 67 or 76) by as few as 1 to 15 amino acid residues, as few as 1 to 10 amino acid residues, such as 6-10, as few as 5, as few as 4, 3, 2, or even 1 amino acid residue.

The constant region of an anti-SEMA4D antibody can be mutated to alter effector function in a number of ways. For example, see U.S. Pat. No. 6,737,056B1 and U.S. Patent Application Publication No. 2004/0132101A1, which disclose Fc mutations that optimize antibody binding to Fc receptors.

In certain anti-SEMA4D antibodies or fragments, variants or derivatives thereof useful in the methods provided herein, the Fc portion can be mutated to decrease effector function using techniques known in the art. For example, the deletion or inactivation (through point mutations or other means) of a constant region domain can reduce Fc receptor binding of the circulating modified antibody thereby increasing tumor localization. In other cases, constant region modifications consistent with the instant invention moderate complement binding and thus reduce the serum half-life. Yet other modifications of the constant region can be used to modify disulfide linkages or oligosaccharide moieties that allow for enhanced localization due to increased antigen specificity or antibody flexibility. The resulting physiological profile, bioavailability and other biochemical effects of the modifications, such as tumor localization, biodistribution and serum half-life, can easily be measured and quantified using well known immunological techniques without undue experimentation.

Anti-SEMA4D antibodies for use in the methods provided herein include derivatives that are modified, e.g., by the covalent attachment of any type of molecule to the antibody such that covalent attachment does not prevent the antibody from specifically binding to its cognate epitope. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications can be carried out by known techniques, including, but not limited to specific chemical cleavage, acetylation, formylation, etc. Additionally, the derivative can contain one or more non-classical amino acids.

A "conservative amino acid substitution" is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity (e.g., the ability to bind an anti-SEMA4D polypeptide, to block SEMA4D interaction with its receptor, or to promote neurogenesis in a subject).

For example, it is possible to introduce mutations only in framework regions or only in CDR regions of an antibody molecule. Introduced mutations can be silent or neutral missense mutations, i.e., have no, or little, effect on an antibody's ability to bind antigen. These types of mutations can be useful to optimize codon usage, or improve a hybridoma's antibody production. Alternatively, non-neutral missense mutations may alter an antibody's ability to bind antigen. One of skill in the art would be able to design and test mutant molecules with desired properties such as no alteration in antigen binding activity or alteration in binding activity (e.g., improvements in antigen binding activity or change in antibody specificity). Following mutagenesis, the encoded protein may routinely be expressed and the functional and/or biological activity of the encoded protein, (e.g., ability to immunospecifically bind at least one epitope of a SEMA4D polypeptide) can be determined using techniques described herein or by routinely modifying techniques known in the art.

In certain embodiments, the anti-SEMA4D antibodies for use in the methods provided herein comprise at least one optimized complementarity-determining region (CDR). By "optimized CDR" is intended that the CDR has been modified and optimized to improve binding affinity and/or anti-SEMA4D activity that is imparted to an anti-SEMA4D antibody comprising the optimized CDR. "Anti-SEMA4D activity" or "SEMA4D blocking activity" can include activity which modulates one or more of the following activities associated with SEMA4D: B cell activation, aggregation and survival; CD40-induced proliferation and antibody production; antibody response to T cell dependent antigens; T cell or other immune cell proliferation; dendritic cell maturation; demyelination and axonal degeneration; apoptosis of pluripotent neural precursors and/or oligodendrocytes; induction of endothelial cell migration; inhibition of spontaneous monocyte migration; binding to cell surface Plexin-B1 or other receptor, or any other activity association with soluble SEMA4D or SEMA4D that is expressed on the surface of SEMA4D+ cells. Anti-SEMA4D activity can also be attributed to a decrease in incidence or severity of diseases associated with SEMA4D expression, including, but not limited to, certain types of cancers including lymphomas, autoimmune diseases, inflammatory diseases including central nervous system (CNS) and peripheral nervous system (PNS) inflammatory diseases, transplant rejections, and invasive angiogenesis. Examples of optimized antibodies based on murine anti-SEMA4D MAbs BD16 and BB18, were described in US Publ. No. 2008/0219971 A1, International Patent Application WO 93/14125 and Herold et al., *Int. Immunol.* 7(1): 1-8 (1995), each of which are herein incorporated by reference in their entirety. The modifications may involve replacement of amino acid residues within the CDR such that an anti-SEMA4D antibody retains specificity for the SEMA4D antigen and has improved binding affinity and/or improved anti-SEMA4D activity.

In certain embodiments, the binding molecule of the application, e.g., an anti-SEMA4D antibody or antigen binding fragment thereof, inhibits SEMA4D activity and/or the interaction of SEMA4D with a SEMA4D receptor or portion thereof. In certain embodiments, the inhibited SEMA4D activity includes one or more of the following: B cell activation, aggregation and/or survival; CD40-induced proliferation and/or antibody production; antibody response to T cell dependent antigens; T cell or other immune cell proliferation; dendritic cell maturation; demyelination and axonal degeneration; apoptosis of pluripotent neural precursors and/or oligodendrocytes; induction of endothelial cell migration; inhibition of spontaneous monocyte migration; SEMA4D dimerization; binding to cell surface Plexin-B1 or other receptor, or any other activity association with soluble SEMA4D or SEMA4D that is expressed on the surface of SEMA4D+ cells.

"Inhibits" as used herein can include partial or complete blocking of, e.g., binding, activity, function, interaction, or other measurable feature.

V. Treatment Methods Using Therapeutic Anti-SEMA4D Antibodies

Methods of the invention are directed to the use of anti-SEMA4D binding molecules, e.g., antibodies, including antigen-binding fragments, variants, and derivatives thereof, to promote neurogenesis in a subject having neurodegenerative disorders, neuroinflammatory disorders, acute brain injuries, and certain CNS dysfunctions. Though the following discussion refers to administration of an anti-SEMA4D antibody, the methods described herein are also applicable to the antigen-binding fragments, variants, and derivatives of these anti-SEMA4D antibodies that retain the desired properties of the anti-SEMA4D antibodies of the invention, e.g., capable of specifically binding SEMA4D, e.g., human, mouse, or human and mouse SEMA4D, having SEMA4D neutralizing activity, and/or blocking the interaction of SEMA4D with its receptor, e.g., Plexin-B1.

In one embodiment, treatment includes the application or administration of an anti-SEMA4D binding molecule, e.g., an antibody or antigen binding fragment thereof as described herein to a patient, where the patient has, or has the risk of developing a neurodegenerative disorders, neuroinflammatory disorders, acute brain injuries, and certain CNS dysfunctions. In another embodiment, treatment is also intended to include the application or administration of a pharmaceutical composition comprising the anti-SEMA4D binding molecule, e.g., an antibody or antigen binding fragment thereof to a patient, where the patient has, or has the risk of developing a neurodegenerative disorders, neuroinflammatory disorders, acute brain injuries, and certain CNS dysfunctions.

In one embodiment, the pharmaceutical composition comprising the anti-SEMA4D binding molecule, e.g., an antibody or antigen binding fragment thereof to a patient, may be delivered in any conventional form, including any form known in the art in which it may pass through the blood brain barrier (i.e., act on the brain side). Due to the interaction of SEMA4D with a receptor on astrocytes, which are brain-resident cells important for the maintenance of blood brain barrier integrity, the application or administration of the anti-SEMA4D binding molecule may occur on the brain side of the blood brain barrier to block the interaction of SEMA4D with its receptor on astrocytes. Methods for allowing factors to pass through the blood-brain barrier include minimizing the size of the factor, providing hydrophobic factors which may pass through more easily, conjugating the modulating agent to a carrier molecule that has a substantial permeability coefficient across the blood brain barrier.

In another embodiment, the pharmaceutical composition comprising the anti-SEMA4D binding molecule, e.g., an antibody or antigen binding fragment thereof to a patient, may be delivered in any conventional form, including any form known in the art in which it may by-pass the blood brain barrier (i.e., act on the blood side). Due to the interaction of SEMA4D with a receptor on endothelial cells, the application or administration of an anti-SEMA4D binding molecule may occur on the blood side of the blood brain barrier. By administering an anti-SEMA4D binding molecule by a route that exposes it to the blood side, e.g. including, but not limited to, intravenous administration, the anti-SEMA4D binding molecule will be permitted to inhibit the interaction of SEMA4D with the SEMA4D receptor or a portion of the receptor that is expressed by the endothelial cells. In another embodiment the blood-brain barrier can be by-passed, for instance, by in vivo transfection of cells with expression vectors containing genes that code for growth factors, so that the cells themselves produce the factor. Any useful genetic modification of the cells is within the scope of the present invention. For example, in addition to genetic modification of the cells to express growth factors, the cells may be modified to express other types of neurological agents such as neurotransmitters. Preferably, the genetic modification is performed either by infection of the cells lining ventricular regions with recombinant retroviruses or transfection using methods known in the art.

The anti-SEMA4D binding molecules, e.g., antibodies or binding fragments thereof as described herein are useful for the treatment of various central nervous system disorders such as neurodegenerative disorders, neuroinflammatory disorders, acute brain injuries, and certain CNS dysfunctions. In some embodiments, treatment of central nervous system disorders such as neurodegenerative disorders, neuroinflammatory disorders, acute brain injuries, and certain CNS dysfunctions is intended to include promotion of neurogenesis. In other embodiments, treatment of central nervous system disorders such as neurodegenerative disorders, neuroinflammatory disorders, acute brain injuries, and certain CNS dysfunctions is intended to include an increasing proliferation of progenitor cells. In other embodiments, treatment of central nervous system disorders such as neurodegenerative disorders, neuroinflammatory disorders, acute brain injuries, and certain CNS dysfunctions is intended to enhance differentiation of progenitor cells. In other embodiments, treatment of central nervous system disorders such as neurodegenerative disorders, neuroinflammatory disorders, acute brain injuries, and certain CNS dysfunctions is intended to increase survival of precursor or progenitor cells.

In one embodiment, the invention relates to the use of anti-SEMA4D binding molecules, e.g., antibodies or antigen-binding fragments, variants, or derivatives thereof, as a medicament, in particular for use in the treatment or prophylaxis of central nervous system disorders such as neurodegenerative disorders, neuroinflammatory disorders, acute brain injuries, and certain CNS dysfunctions to promote neurogenesis by increasing proliferation, enhancing differentiation, and/or increasing survival of precursor or progenitor cells. In certain embodiments, the method of the application increase the number of, enhances differentiation of, and/or increases survival of progenitor cells.

In accordance with the methods of the present invention, at least one anti-SEMA4D binding molecule, e.g., an antibody or antigen binding fragment, variant, or derivative thereof, as defined elsewhere herein can be used to promote a positive therapeutic response with respect to the central nervous system disorders such as neurodegenerative disorders, neuroinflammatory disorders, acute brain injuries, and certain CNS dysfunctions.

A "positive therapeutic response" with respect to the central nervous system disorder is intended to include an improvement in the disease in association with the anti-inflammatory activity, anti-angiogenic activity, anti-apoptotic activity, or the like, of these antibodies, and/or an improvement in the symptoms associated with the disease. That is, an anti-proliferative effect, the prevention of further proliferation of the SEMA4D-expressing cell or the cell expressing receptor for SEMA4D, a reduction in the inflammatory response including but not limited to reduced secretion of inflammatory cytokines, adhesion molecules, proteases, immunoglobulins (in instances where the SEMA4D or SEMA4D receptor bearing cell is a B cell), combinations thereof, and the like, increased production of anti-inflammatory proteins, a reduction in the number of autoreactive cells, an increase in immune tolerance, inhibition of autoreactive cell survival, reduction in apoptosis, reduction in endothelial cell migration, increase in spontaneous monocyte migration, reduction in and/or a decrease in one or more symptoms mediated by stimulation of sSEMA4D or SEMA4D-expressing cells can be observed. Such positive therapeutic responses are not limited to the route of administration and may comprise administration to the donor, the donor tissue (such as for example organ perfusion), the host, any combination thereof, and the like. In particular, the methods provided herein are directed to inhibiting, preventing, reducing, alleviating, or lessening the development of a neuroinflammatory disorder in a patient. Thus, for example, an improvement in the disease may be characterized as an absence of clinically observable symptoms, an increase in proliferation, differentiation, and/or survival of precursor or progenitor cells. The anti-SEMA4D binding molecules, e.g., antibodies or antigen binding fragments, variants, or derivatives thereof can be used in combination with at least one or more other treatments for neuroinflammatory disorders; where the additional therapy is administered prior to, during, or subsequent to the anti-SEMA4D binding molecule, e.g., antibody or antigen binding fragment, variant, or derivative thereof, therapy. Thus, where the combined therapies comprise administration of an anti-SEMA4D binding molecule, e.g., an antibody or antigen binding fragment, variant, or derivative thereof, in combination with administration of another therapeutic agent, the methods of the invention encompass coadministration, using separate formulations or a single pharmaceutical formulation, with simultaneous or consecutive administration in either order.

VI. Pharmaceutical Compositions and Administration Methods

Methods of preparing and administering anti-SEMA4D binding molecules, e.g., antibodies, or antigen-binding fragments, variants, or derivatives thereof to a subject in need thereof are well known to or are readily determined by those skilled in the art. The route of administration of the anti-SEMA4D binding molecule, e.g, antibody, or antigen-binding fragment, variant, or derivative thereof, can be, for example, oral, parenteral, by inhalation or topical. The term parenteral as used herein includes, e.g., intravenous, intraarterial, intraperitoneal, intramuscular, subcutaneous, rectal, or vaginal administration. While all these forms of administration are clearly contemplated as being within the scope of the invention, an example of a form for administration would be a solution for injection, in particular for intravenous or intraarterial injection or drip. A suitable pharmaceutical composition for injection can comprise a buffer (e.g. acetate, phosphate or citrate buffer), a surfactant (e.g. polysorbate), optionally a stabilizer agent (e.g. human albumin), etc. However, in other methods compatible with the teachings herein, anti-SEMA4D binding molecules, e.g., antibodies, or antigen-binding fragments, variants, or derivatives thereof can be delivered directly to the site of the adverse cellular population thereby increasing the exposure of the diseased tissue to the therapeutic agent.

As discussed herein, anti-SEMA4D binding molecules, e.g., antibodies, or antigen-binding fragments, variants, or derivatives thereof can be administered in a pharmaceutically effective amount for the in vivo treatment of neuroinflammatory disorders. In this regard, it will be appreciated that the disclosed binding molecules can be formulated so as to facilitate administration and promote stability of the active agent. In certain embodiments, pharmaceutical compositions in accordance with the present invention comprise a pharmaceutically acceptable, non-toxic, sterile carrier such as physiological saline, non-toxic buffers, preservatives and the like. For the purposes of the instant application, a pharmaceutically effective amount of an anti-SEMA4D binding molecule, e.g., an antibody, or antigen-binding fragment, variant, or derivative thereof, shall be held to mean an amount sufficient to achieve effective binding to a target and to achieve a benefit, e.g., to promote neurogenesis in a subject having central nervous system disorders such as neurodegenerative disorders, neuroinflammatory disorders, acute brain injuries, and certain CNS dysfunctions.

The pharmaceutical compositions used in this invention comprise pharmaceutically acceptable carriers, including, e.g., ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol, and wool fat.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include, e.g., water, alcoholic/aqueous solutions, emulsions or suspensions, including saline and buffered media. In the subject invention, pharmaceutically acceptable carriers include, but are not limited to, 0.01-0.1 M and preferably 0.05 M phosphate buffer or 0.8% saline. Other common parenteral vehicles include sodium phosphate solutions, Ringer's dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present such as, for example, antimicrobials, antioxidants, chelating agents, and inert gases and the like.

More particularly, pharmaceutical compositions suitable for injectable use include sterile aqueous solutions (where water soluble) or dispersions and sterile powders for the extemporaneous preparation of sterile injectable solutions or dispersions. In such cases, the composition must be sterile and should be fluid to the extent that easy syringability exists. It should be stable under the conditions of manufacture and storage and will preferably be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Suitable formulations for use in the therapeutic methods disclosed herein are described in Remington's Pharmaceutical Sciences (Mack Publishing Co.) 16th ed. (1980).

Prevention of the action of microorganisms can be achieved by various antibacterial and antifungal agents, for example, parabens, chlorobutanol, phenol, ascorbic acid, thimerosal and the like. In many cases, it will be preferable to include isotonic agents, for example, sugars, polyalcohols, such as mannitol, sorbitol, or sodium chloride in the composition. Prolonged absorption of the injectable compositions can be brought about by including in the composition an agent which delays absorption, for example, aluminum monostearate and gelatin.

In any case, sterile injectable solutions can be prepared by incorporating an active compound (e.g., an anti-SEMA4D antibody, or antigen-binding fragment, variant, or derivative thereof, by itself or in combination with other active agents) in the required amount in an appropriate solvent with one or a combination of ingredients enumerated herein, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yields a powder of an active ingredient plus any additional desired ingredient from a previously sterile-filtered solution thereof. The preparations for injections are processed, filled into containers such as ampoules, bags, bottles, syringes or vials, and sealed under aseptic conditions according to methods known in the art. Further, the preparations may be packaged and sold in the form of a kit. Such articles of manufacture can have labels or package inserts indicating that the associated compositions are useful for treating a subject suffering from, or predisposed to a disease or disorder.

Parenteral formulations can be a single bolus dose, an infusion or a loading bolus dose followed with a maintenance dose. These compositions can be administered at specific fixed or variable intervals, e.g., once a day, or on an "as needed" basis.

Certain pharmaceutical compositions used in this invention can be orally administered in an acceptable dosage form including, e.g., capsules, tablets, aqueous suspensions or solutions. Certain pharmaceutical compositions also can be administered by nasal aerosol or inhalation. Such compositions can be prepared as solutions in saline, employing benzyl alcohol or other suitable preservatives, absorption promoters to enhance bioavailability, and/or other conventional solubilizing or dispersing agents.

The amount of an anti-SEMA4D binding molecule, e.g., antibody, or fragment, variant, or derivative thereof, to be combined with the carrier materials to produce a single dosage form will vary depending upon the host treated and the particular mode of administration. The composition can be administered as a single dose, multiple doses or over an established period of time in an infusion. Dosage regimens also can be adjusted to provide the optimum desired response (e.g., a therapeutic or prophylactic response).

In keeping with the scope of the present disclosure, anti-SEMA4D antibodies, or antigen-binding fragments, variants, or derivatives thereof can be administered to a human or other animal in accordance with the aforementioned methods of treatment in an amount sufficient to produce a therapeutic effect. The anti-SEMA4D antibodies, or antigen-binding fragments, variants or derivatives thereof can be administered to such human or other animal in a conventional dosage form prepared by combining the antibody of the invention with a conventional pharmaceutically acceptable carrier or diluent according to known techniques. It will be recognized by one of skill in the art that the form and character of the pharmaceutically acceptable carrier or diluent is dictated by the amount of active ingredient with which it is to be combined, the route of administration and other well-known variables. Those skilled in the art will further appreciate that a cocktail comprising one or more species of anti-SEMA4D binding molecules, e.g., antibodies, or antigen-binding fragments, variants, or derivatives thereof, of the invention can be used.

By "therapeutically effective dose or amount" or "effective amount" is intended an amount of anti-SEMA4D binding molecule, e.g., antibody or antigen binding fragment, variant, or derivative thereof, that when administered brings about a positive therapeutic response with respect to treatment of a patient with a disease to be treated, e.g., increasing proliferation, enhancing differentiation, and/or increasing survival of precursor or progenitor cells.

Therapeutically effective doses of the compositions of the present invention, for the promotion of neurogenesis vary depending upon many different factors, including means of administration, target site, physiological state of the patient, whether the patient is human or an animal, other medications administered, and whether treatment is prophylactic or therapeutic. In certain embodiments the patient is a human, but non-human mammals including transgenic mammals can also be treated. Treatment dosages may be titrated using routine methods known to those of skill in the art to optimize safety and efficacy.

The amount of at least one anti-SEMA4D binding molecule, e.g., antibody or binding fragment, variant, or derivative thereof, to be administered is readily determined by one of ordinary skill in the art without undue experimentation given the disclosure of the present invention. Factors influencing the mode of administration and the respective amount of at least one anti-SEMA4D binding molecule, e.g., antibody, antigen-binding fragment, variant or derivative thereof include, but are not limited to, the severity of the disease, the history of the disease, and the age, height, weight, health, and physical condition of the individual undergoing therapy. Similarly, the amount of anti-SEMA4D binding molecule, e.g., antibody, or fragment, variant, or derivative thereof, to be administered will be dependent upon the mode of administration and whether the subject will undergo a single dose or multiple doses of this agent.

The invention also provides for the use of an anti-SEMA4D binding molecule, e.g., antibody of the invention, or antigen-binding fragment, variant, or derivative thereof, in the manufacture of a medicament for treating a subject for treating a neuroinflammatory disorder, wherein the medicament is used in a subject that has been pretreated with at least one other therapy. By "pretreated" or "pretreatment" is intended the subject has received one or more other therapies (e.g., been treated with at least one other neuroinflammatory therapy) prior to receiving the medicament comprising the anti-SEMA4D binding molecule, e.g., antibody or antigen-binding fragment, variant, or derivative thereof "Pretreated" or "pretreatment" includes subjects that have been treated with at least one other therapy within 2 years, within 18 months, within 1 year, within 6 months, within 2 months, within 6 weeks, within 1 month, within 4 weeks, within 3 weeks, within 2 weeks, within 1 week, within 6 days, within 5 days, within 4 days, within 3 days, within 2 days, or even within 1 day prior to initiation of treatment with the medicament comprising the anti-SEMA4D binding molecule, for example, the monoclonal antibody VX15/2503 disclosed herein, or antigen-binding fragment, variant, or derivative thereof. It is not necessary that the subject was a responder to pretreatment with the prior therapy or therapies. Thus, the subject that receives the medicament comprising the anti-SEMA4D binding molecule, e.g., an antibody or antigen-binding fragment, variant, or derivative thereof could have responded, or could have failed to respond, to pretreatment with the prior therapy, or to one or more of the prior therapies where pretreatment comprised multiple therapies.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Sambrook et al., ed. (1989) Molecular Cloning A Laboratory Manual (2nd ed.; Cold Spring Harbor Laboratory Press); Sambrook et al., ed. (1992) Molecular Cloning: A Laboratory Manual, (Cold Springs Harbor Laboratory, NY); D. N. Glover ed., (1985) DNA Cloning, Volumes I and II; Gait, ed. (1984) Oligonucleotide Synthesis; Mullis et al. U.S. Pat. No. 4,683,195; Hames and Higgins, eds. (1984) Nucleic Acid Hybridization; Hames and Higgins, eds. (1984) Transcription And Translation; Freshney (1987) Culture Of Animal Cells (Alan R. Liss, Inc.); Immobilized Cells And Enzymes (IRL Press) (1986); Perbal (1984) A Practical Guide To Molecular Cloning; the treatise, Methods In Enzymology (Academic Press, Inc., N.Y.); Miller and Calos eds. (1987) Gene Transfer Vectors For Mammalian Cells, (Cold Spring Harbor Laboratory); Wu et al., eds., Methods In Enzymology, Vols. 154 and 155; Mayer and Walker, eds. (1987) Immunochemical Methods In Cell And Molecular Biology (Academic Press, London); Weir and Blackwell, eds., (1986) Handbook Of Experimental Immunology, Volumes I-IV; Manipulating the Mouse Embryo, Cold Spring Harbor Laboratory Press, Cold Spring Harbor, N.Y., (1986); and in Ausubel et al. (1989) Current Protocols in Molecular Biology (John Wiley and Sons, Baltimore, Md.).

General principles of antibody engineering are set forth in Borrebaeck, ed. (1995) Antibody Engineering (2nd ed.; Oxford Univ. Press). General principles of protein engineering are set forth in Rickwood et al., eds. (1995) Protein Engineering, A Practical Approach (IRL Press at Oxford Univ. Press, Oxford, Eng.). General principles of antibodies and antibody-hapten binding are set forth in: Nisonoff (1984) Molecular Immunology (2nd ed.; Sinauer Associates, Sunderland, Mass.); and Steward (1984) Antibodies, Their Structure and Function (Chapman and Hall, New York, N.Y.). Additionally, standard methods in immunology known in the art and not specifically described are generally followed as in Current Protocols in Immunology, John Wiley & Sons, New York; Stites et al., eds. (1994) Basic and Clinical Immunology (8th ed; Appleton & Lange, Norwalk, Conn.) and Mishell and Shiigi (eds) (1980) Selected Methods in Cellular Immunology (W.H. Freeman and Co., NY).

Standard reference works setting forth general principles of immunology include Current Protocols in Immunology, John Wiley & Sons, New York; Klein (1982) J., Immunology: The Science of Self-Nonself Discrimination (John Wiley & Sons, NY); Kennett et al., eds. (1980) Monoclonal Antibodies, Hybridoma: A New Dimension in Biological Analyses (Plenum Press, NY); Campbell (1984) "Monoclonal Antibody Technology" in Laboratory Techniques in Biochemistry and Molecular Biology, ed. Burden et al., (Elsevere, Amsterdam); Goldsby et al., eds. (2000) Kuby Immunnology (4th ed.; H. Freemand & Co.); Roitt et al. (2001) Immunology (6th ed.; London: Mosby); Abbas et al. (2005) Cellular and Molecular Immunology (5th ed.; Elsevier Health Sciences Division); Kontermann and Dubel (2001) Antibody Engineering (Springer Verlan); Sambrook and Russell (2001) Molecular Cloning: A Laboratory Manual (Cold Spring Harbor Press); Lewin (2003) Genes VIII (Prentice Hall 2003); Harlow and Lane (1988) Antibodies: A Laboratory Manual (Cold Spring Harbor Press); Dieffenbach and Dveksler (2003) PCR Primer (Cold Spring Harbor Press).

All of the references cited above, as well as all references cited herein, are incorporated herein by reference in their entireties.

The following examples are offered by way of illustration and not by way of limitation.

EXAMPLES

Example 1: Experimental Design

The basic experimental design is shown in FIG. 1. Male, 6 week-old, CB-17/lcr-1/1Jcl mice ("CB-17 mice") were used to evaluate the effect of anti-SEMA4D antibodies on neurogenesis following stroke injury. The mice were subjected to middle cerebral artery (MCA) occlusion (MCAO). In brief, animals were placed under deep anesthesia induced with 4% halothane in a 30% oxygen/70% nitrous oxide mixture, and the anesthetic plane was maintained with 1-2% halothane. Permanent focal cerebral ischemia was produced by ligation and disconnection of the distal portion of the left middle cerebral artery (MCA) as described elsewhere (Taguchi et al., 2004, 2007). The left MCA was isolated, electrocauterized, and disconnected just distal to crossing the olfactory tract (distal M1 portion) with animals under halothane anesthesia. Cerebral blood flow (CBF) in the MCA area was monitored as described previously (Matsushita et al., 1998). Cerebral infarction produced in this mouse strain is highly reproducible and limited to the ipsilateral cerebral cortex (Taguchi et al., 2004, 2007).

Following the occlusion, the mice were divided into two groups: the treatment group was injected with anti-SEMA4D antibody MAb 67-2 and the control group was injected with IgG isotype control MAb 2B8. Mice received 0.6 mg/kg of monoclonal antibody via intraperitoneal (IP) injection at 1 hour, 3 hours, 3 days, 7 days, 14 days and 21 days after MCAO.

At day 7 following MCAO, a subset of animals from each antibody-injected cohort was sacrificed, brains extracted, and tissues analyzed by immunohistochemistry and reverse transcription-polymerase chain reaction (RT-PCR).

For immunohistochemical analyses of brain sections, animals were perfused with a 2% paraformaldehyde-lysine-periodate (PLP) fixative (0.75 M lysine-HCl/0.01 M periodate/0.075 M phosphate buffer), and the brains were cut into 20-μm-thick serial sections on a cryostat. Brain sections were treated with 0.1% $H_2O_2$ for quenching, washed in phosphate-buffered saline (PBS), and incubated overnight with one or more of the following primary antibodies: anti-NeuN for neurons, anti-Nestin and anti-Sox2 for neural stem/precursor cells in dilution buffer (0.3% Triton-X-100/5% horse serum/PBS). After being washed three times in PBS, the sections were incubated with the appropriate secondary antibodies for 3 hours, and for NeuN staining, were then visualized by the ABC reaction using the peroxidase ABC Elite Kit (Vector Laboratories, Burlingame, Calif.) with diaminobenzidine (DAB; Sigma). For Nestin/Sox2 double immunocytochemistry, FITC- (Sox2) and Cy3-labeled (Nestin) secondary antibodies were used. Fluorescent photomicrographs were obtained with a laser confocal microscope. The results are shown in FIG. 2A-E and discussed in detail below.

For RT-PCR analyses, total RNA was isolated from microdissected brain tissue at day 7 post-MCAO and cDNA prepared. cDNA was PCR-amplified under the following conditions: 15 s at 94° C., 30 s at 56° C., and 1 min at 68° C. (40 cycles). Primer sequences were as follows: nestin forward, CACTAGAAAGCAGGAACCAG (SEQ ID NO:11) and nestin reverse, AGATGGTTCACAATCCTCTG (SEQ ID NO:12) (amplicon size, 307 bp); Sox2 forward, TTGGGAGGGGTGCAAAAAGA (SEQ ID NO:13) and Sox2 reverse, CCTGCGAAGCGCTAACGTA (SEQ ID NO:14) (amplicon size, 312 bp); proteolipid protein (PLP) forward, TGAGCGCAACGGTAACAGG (SEQ ID NO:15) and PLP reverse, GGGAGAACACCATACATTCTGG (SEQ ID NO:16) (amplicon size, 295 bp); and β-actin forward, GCTCGTCGTCGACAAGGGCTC (SEQ ID NO:17) and β-actin reverse, CAAACATGATCTGGGTCATCTTCTC (SEQ ID NO:18) (amplicon size, 353 bp). The results are shown in FIG. 3A-D and discussed in detail below.

Behavioral assessments were performed on the remaining cohorts of mice on days 14 and 30 following MCAO. To assess cortical function, mice were analyzed by behavioral testing using the open field task. Briefly, animals were allowed to search freely in a square acrylic box (30×3×30 cm) for 20 minutes. A light source on the ceiling of the enclosure was on during the first 10 min (light period) and off during a subsequent 10-min period (dark period). On the X- and Y-banks of the open field, two infrared beams were mounted 2 cm above the floor, spaced with at 10-cm intervals, forming a flip-flop circuit between them. The total number of beam crossings by the animal was counted and scored as traveling behavior (locomotion). The results are shown in FIG. 6A-C and discussed in detail below.

On day 30 following MCAO, the remaining cohorts of mice were sacrificed and brains processed for NeuN immunohistochemistry. Mice were perfused transcardially with 4% paraformaldehyde, brains were removed, and coronal sections (14 μm) were stained with mouse antibody to NeuN, followed by reaction with biotinylated goat anti-mouse IgG (Chemicon, Temecula, Calif.; 1/500), ABC Elite Kit (Vector Laboratories, Burlingame, Calif.), and DAB (Sigma) as chromogen. The area of the ipsilateral and contralateral cerebral hemisphere occupied by the neuronal nuclear marker NeuN was measured using Image J. Ipsilateral and contralateral cerebral hemisphere volume was calculated by integrating coronally oriented ipsilateral and contralateral cerebral hemisphere area. Involution of ipsilateral cerebral hemisphere volume was calculated as (ipsilateral/contralateral cerebral hemisphere volume). The results are shown in FIG. 4A-D and FIG. 5A-B and discussed in detail below.

Figure 2:
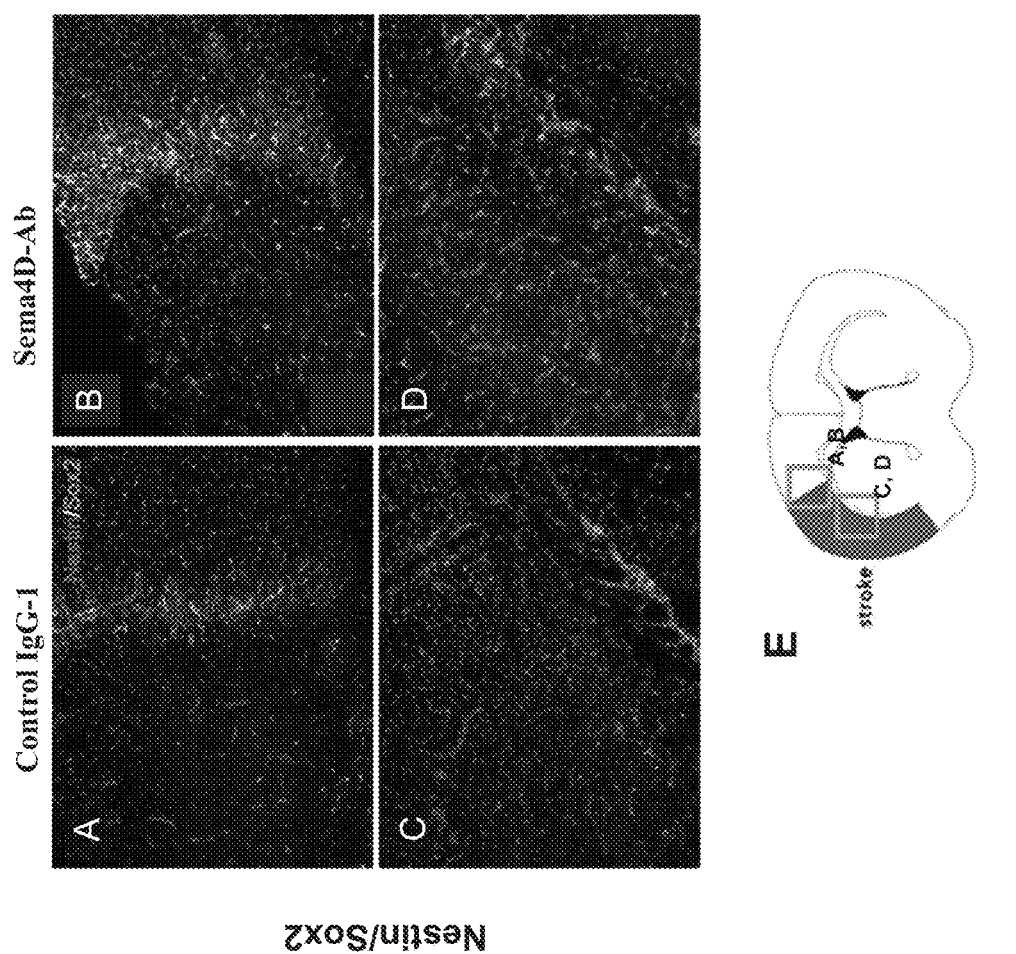
Figures 3A, 3B, 3C, 3D:
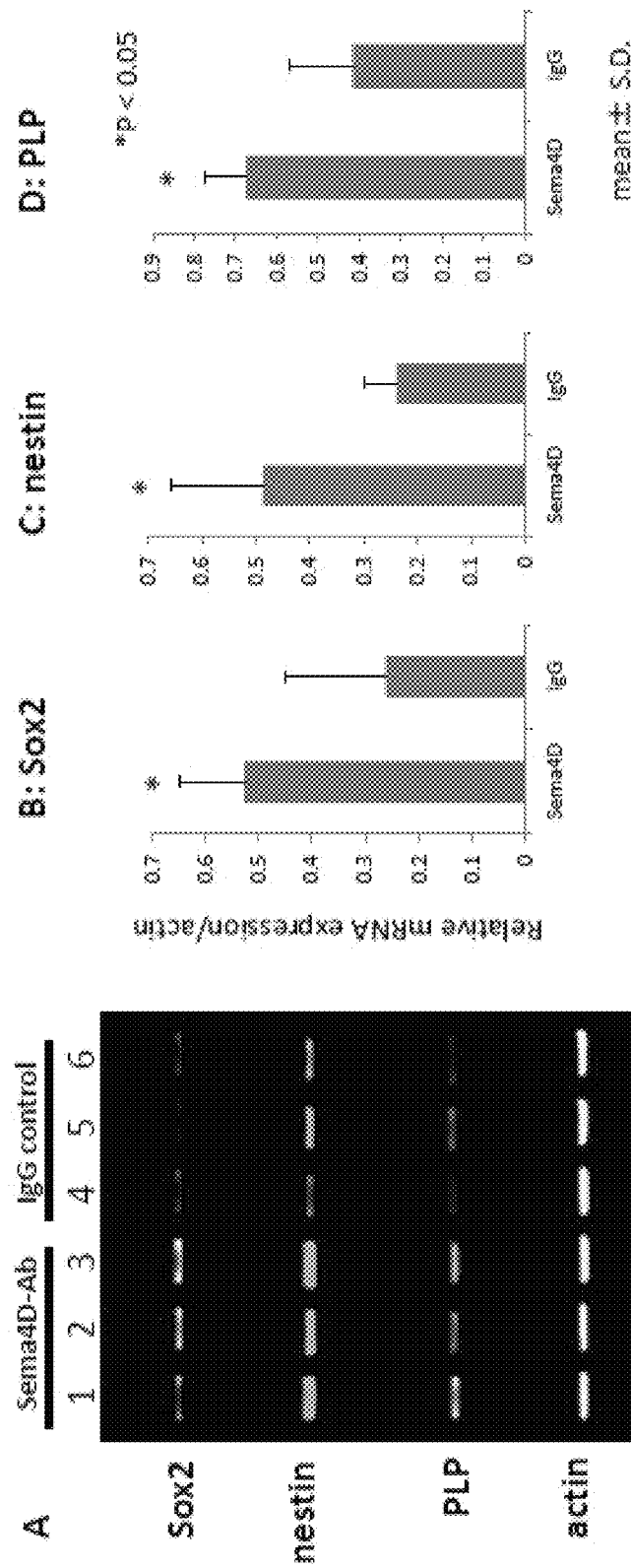

Example 2: Effect of Anti-SEMA4D Antibody on the Presence of Neural Stem/Precursor Cells in MCAO Brain At 7 days after MCAO, the effect of anti-SEMA4D antibody on the presence of neural stem/precursor cells was examined. FIG. 2 shows images of immunocytochemical staining of ischemic tissue from 2 representative areas in the border of infarction (symbolized in FIG. 2E) of isotype control (left panels, A and C) and anti-SEMA4D antibody-treated mice (right panels, B and D). These results show that mice treated with anti-SEMA4D antibody have increased expression of neural stem/progenitor cell marker proteins as compared to mice treated with control antibody. These data suggests that anti-SEMA4D antibody may protect neural stem/precursor cell populations and/or induce neurogenesis in the ischemic brain.

The mRNA expression of neural stem/precursor cells in mice treated with anti-SEMA4D antibody and isotype control was detected by conventional RT-PCR in the ischemic tissue on day 7 after MCAO. These results are shown in FIGS. 3A-D. The results show a significant increase ($p<0.05$) in expression of Sox2, nestin and PLP relative to the housekeeping gene, β-actin, in mice treated with anti-SEMA4D antibody as compared to those treated with isotype control antibody. Since Sox2 and nestin are markers for neural stem/precursor cells, increased expression of these markers following treatment with anti-SEMA4D antibody suggests that anti-SEMA4D antibody may promote neurogenesis. An increase in neurogenesis observed after anti-SEMA4D treatment in the ischemic brain could be a result of increased proliferation of neural stem/precursor cells, and/or increased survival of newly formed neural stem/precursor cells.

Example 3: Effect of Anti-SEMA4D Antibody on Brain Volume After Cerebral Infarction At 30 days after MCAO, the effect of anti-SEMA4D antibody on the volume of the brain was examined. FIGS. 4A-4B show brain sections stained with an antibody specific for the mature neuronal marker, NeuN, from 1 representative isotype control mouse (left, 4A) and 1 representative anti-SEMA4D antibody-treated mouse (right, 4B). Brain volume is represented by the volume of the striatum (solid line) and the hemisphere (dotted line). FIGS. 4C-4D show the calculated ratio (L/R) of striatum and hemisphere volume, respectively, for each group of treated mice. While there is no statistically significant difference in the total hemispheric volume of the brains (dashed line) between mice treated with anti-SEMA4D antibody and those treated with isotype control, mice treated with anti-SEMA4D antibody have significantly larger striatal volume (solid line) than mice treated with control antibody. These data suggest that striatal regions proximal to the focal ischemic insult may be protected by anti-SEMA4D antibody treatment.

Figure 5:
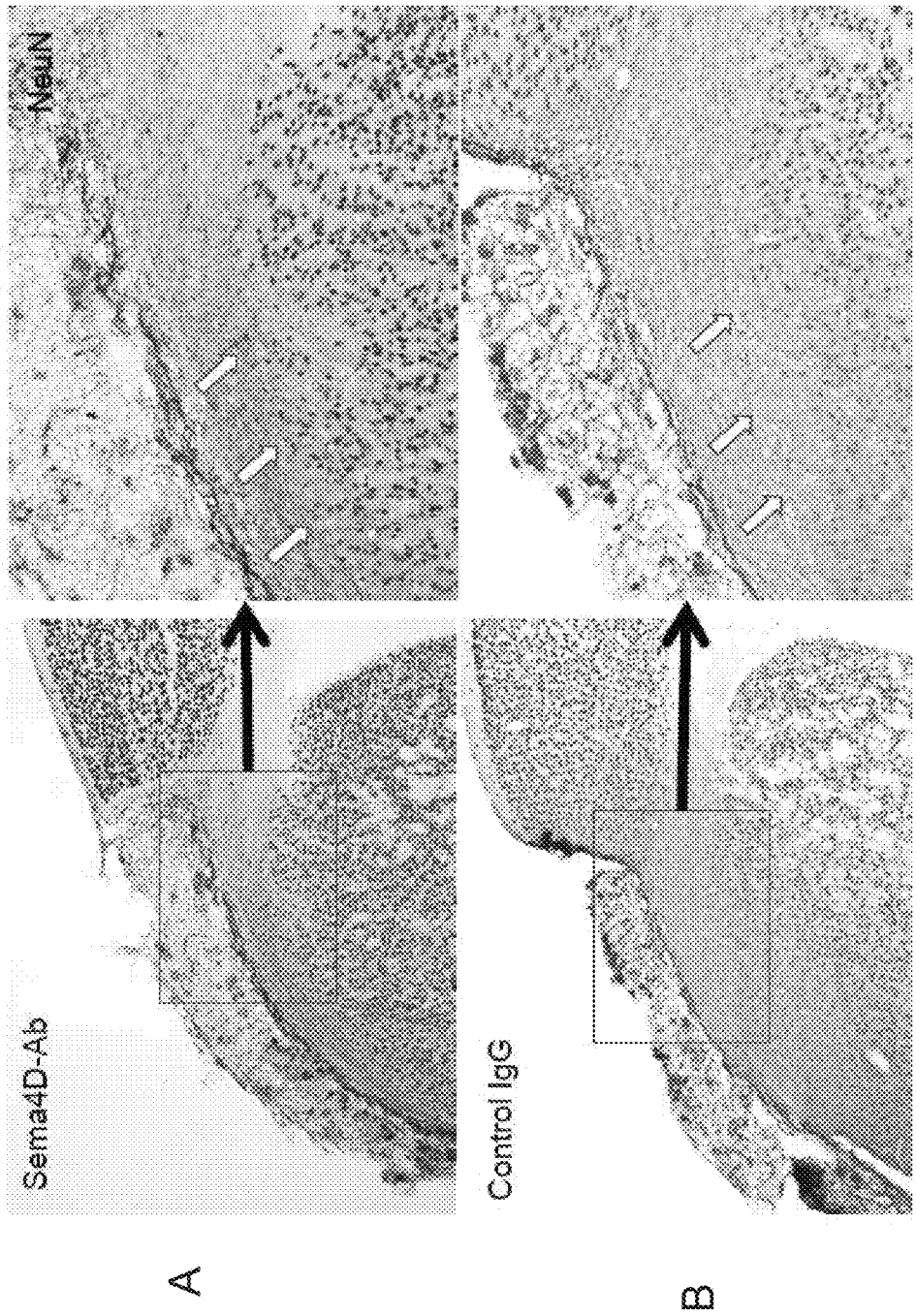

Example 4: Effect of Anti-SEMA4D Antibody on the Presence of Neurons in MCAO Brain At 30 days after MCAO, the effect of anti-SEMA4D antibody on the presence of neurons in the brain was examined. FIG. 5 shows NeuN-stained images of ischemic brain tissue from 1 representative isotype control mouse (bottom panels, 5B) and 1 representative anti-SEMA4D antibody-treated mouse (top panels, 5A). These results show that mice treated with anti-SEMA4D antibody have increased expression of the mature neuronal cell marker, NeuN, in the striatum at the border of cerebral infarction (arrows), when compared to mice treated with control antibody. These data suggest that anti-SEMA4D antibody treatment promotes the development of mature neurons, potentially by protecting neural stem/precursor cell populations and/or inducing neurogenesis in the ischemic brain.

Example 5: Effect of Anti-SEMA4D Antibody on Behavioral Activity of MCAO Mice

At 30 days after MCAO, the effect of anti-SEMA4D antibody on behavioral activity was examined. Mice treated with anti-SEMA4D antibody and control IgG were subjected to an open-field test for 10 minutes under the light and dark environment. FIGS. 6A-6B show how mice undergoing MCAO (both control IgG and anti-SEMA4D antibody treated mice) have significantly higher activity in light phase (p<0.05) compared to sham-treated mice, but not in dark phase. Mice usually have increased activity when they are put into the dark from the light environment. FIG. 6C shows that the ratio of dark/light phase locomotion activity was significantly improved in mice treated with anti-SEMA4D antibody, comparable to sham-treated mice, in contrast to mice treated with control antibody (p<0.05). The dark/light phase ratios were not significantly different between the anti-SEMA4D and sham surgery group. These results suggest that anti-SEMA4D antibody treatment of MCAO-lesioned mice may act to normalize their responses to dark/light stimuli, while the mice receiving control IgG appear to maintain abnormal dark/light activity typically exhibited by MCAO-lesioned mice.

Example 6: Effect of Anti-SEMA4D Antibody on Blood Brain Barrier Integrity and Neurogenesis Another study will be conducted to assess the effect(s) of anti-SEMA4D on blood-brain barrier (BBB integrity) and neurogenesis in a rat model of permanent middle cerebral artery occlusion (MCAO).

The basic experimental design is shown in FIG. 7. The rats will be subjected to middle cerebral artery (MCA) occlusion (MCAO). Following the occlusion, the rats will be divided into three groups of 15 rats: a treatment group will be injected with anti-SEMA4D antibody MAb 67-2, a control group will be injected with IgG isotype control MAb 2B8, and a non-MCAO group will be injected with IgG isotype control MAb 2B8. Rats will receive 15.0 mg/kg of monoclonal antibody via intraperitoneal (IP) injection at 1 hour, 3 days, 7 days, 14 days and 21 days after MCAO. Blood samples will be taken periodically for later assessment of drug levels. Rats will receive scheduled antibody injections and will undergo behavioral testing (cylinder test and limb placing test) over a 4-week timeframe.

Magnetic resonance imaging (MRI) will be used to assess the BBB integrity of 5 randomly selected rats from each treatment group. Another subset of rats (i.e., 5 rats) will receive i.p. BrdU injections on Days 4-6 to label neuroprogenitor cells. At termination, the subset of rats receiving BrdU will be perfused with 4% paraformaldehyde and brains extracted. The third subset of rats will be perfused with saline, brains microdissected, and tissue fresh-frozen. Extracted brains/microdissected tissues will undergo immunohistochemical and biochemical assessment of microglial activation and neurogenesis.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims and list of embodiments disclosed herein. Although specific terms are employed herein, they are used in a generic and descriptive sense only and not for purposes of limitation.

What is claimed is:

1. A method for regenerating neurons in a subject comprising administering to a subject in need of neural regeneration as a result of stroke an effective amount of an isolated antibody or an antigen-binding fragment thereof that comprises
a variable domain of a heavy chain (VH) comprising the VH-CDR1, VH-CDR2, and VH-CDR3 amino acid sequences SEQ ID NOs: 5, 6, and 7, respectively, and
a variable domain of a light chain (VL) comprising the VL-CDR1, VL-CDR2, and VL-CDR3 amino acid sequences SEQ ID NOs: 8, 9, and 10, respectively,
wherein the antibody or fragment thereof specifically binds to semaphorin-4D (SEMA4D) and
wherein the subject exhibits an increase in one or more of proliferation, differentiation, or migration of neural progenitor cells.

2. The method of claim 1, wherein the antibody or fragment thereof is administered to the blood side of the blood brain barrier.

3. The method of claim 1, wherein the antibody or fragment thereof is administered to the brain side of the blood brain barrier.

4. The method of claim 1, wherein the subject exhibits an increase in differentiation of neural progenitor cells.

5. The method of claim 1, wherein the antibody or fragment thereof comprises a VH having the sequence set forth in SEQ ID NO: 1 and a VL having the sequence set forth in SEQ ID NO: 2.

6. The method of claim 1, wherein the antibody or fragment thereof comprises a VH having the sequence set forth in SEQ ID NO: 3 and a VL having the sequence set forth in SEQ ID NO: 4.

7. The method of claim 1 wherein the subject exhibits an increase in expression of a neural precursor or progenitor cell marker.

8. The method of claim 7, wherein the marker is Sox2 and/or nestin.

9. The method of claim 1, wherein the antibody or antigen-binding fragment thereof is IgG isotype.

10. A method for regenerating neurons and increasing striatal brain volume in a subject comprising administering to a subject in need of neural regeneration and increased striatal brain volume as a result of stroke an effective amount of an isolated antibody or an antigen-binding fragment thereof that comprises
a variable domain of a heavy chain (VH) comprising the VH-CDR1, VH-CDR2, and VH-CDR3 amino acid sequences SEQ ID NOs: 5, 6, and 7, respectively, and
a variable domain of a light chain (VL) comprising the VL-CDR1, VL-CDR2, and VL-CDR3 amino acid sequences SEQ ID NOs: 8, 9, and 10, respectively,
wherein the antibody or fragment thereof specifically binds to semaphorin-4D (SEMA4D) and
wherein the subject exhibits an increase in striatal brain volume and one or more of proliferation, differentiation, or migration of neural progenitor cells.

* * * * *

SEQUENCE LISTING

```
<160> NUMBER OF SEQ ID NOS: 18

<210> SEQ ID NO 1
<211> LENGTH: 118
<212> TYPE: PRT
<213> ORGANISM: Artificial Sequence
<220> FEATURE:
<223> OTHER INFORMATION: MAb 67 VH

<400> SEQUENCE: 1

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Ser Asp Tyr
                20                  25                  30

Tyr Met His Trp Val Lys Gln Ser Pro Glu Asn Ser Leu Glu Trp Ile
            35                  40                  45

Gly Gln Ile Asn Pro Thr Thr Gly Gly Ala Ser Tyr Asn Gln Lys Phe
        50                  55                  60

Lys Gly Lys Ala Thr Leu Thr Val Asp Lys Ser Ser Ser Thr Ala Tyr
65                  70                  75                  80

Met Gln Leu Lys Ser Leu Thr Ser Glu Glu Ser Ala Val Tyr Tyr Cys
                85                  90                  95

Thr Arg Tyr Tyr Tyr Gly Arg His Phe Asp Val Trp Gly Gln Gly Thr
                100                 105                 110

Thr Val Thr Val Ser Ser
            115

<210> SEQ ID NO 2
<211> LENGTH: 111
<212> TYPE: PRT
<213> ORGANISM: Artificial Sequence
```

```
<220> FEATURE:
<223> OTHER INFORMATION: MAb 67 VK

<400> SEQUENCE: 2

Asp Ile Val Met Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
                20                  25                  30

Gly Asp Ser Tyr Met Asn Trp Tyr Gln Gln Lys Pro Gly Gln Pro Pro
            35                  40                  45

Lys Leu Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Ser Asn
                85                  90                  95

Glu Asp Pro Tyr Thr Phe Gly Gly Gly Thr Lys Leu Glu Ile Lys
            100                 105                 110

<210> SEQ ID NO 3
<211> LENGTH: 118
<212> TYPE: PRT
<213> ORGANISM: Artificial Sequence
<220> FEATURE:
<223> OTHER INFORMATION: MAb 2503 H2160

<400> SEQUENCE: 3

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Ser Asp Tyr
                20                  25                  30

Tyr Met His Trp Val Arg Gln Ala Pro Gly Gln Gly Leu Glu Trp Met
            35                  40                  45

Gly Gln Ile Asn Pro Thr Thr Gly Gly Ala Ser Tyr Asn Gln Lys Phe
    50                  55                  60

Lys Gly Lys Ala Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Tyr Tyr Gly Arg His Phe Asp Val Trp Gly Gln Gly Thr
            100                 105                 110

Thr Val Thr Val Ser Ser
        115

<210> SEQ ID NO 4
<211> LENGTH: 111
<212> TYPE: PRT
<213> ORGANISM: Artificial Sequence
<220> FEATURE:
<223> OTHER INFORMATION: MAb 2503 L553

<400> SEQUENCE: 4

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Ser Val Asp Tyr Asp
                20                  25                  30

Gly Asp Ser Tyr Met Asn Trp Tyr Gln Gln Lys Pro Gly Gln Pro Pro
            35                  40                  45
```

```
Lys Leu Leu Ile Tyr Ala Ala Ser Asn Leu Glu Ser Gly Val Pro Asp
 50                  55                  60

Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln Gln Ser Asn
                 85                  90                  95

Glu Asp Pro Tyr Thr Phe Gly Gln Gly Thr Lys Leu Glu Ile Lys
            100                 105                 110

<210> SEQ ID NO 5
<211> LENGTH: 10
<212> TYPE: PRT
<213> ORGANISM: Artificial Sequence
<220> FEATURE:
<223> OTHER INFORMATION: Polypeptide anti-CD100 VH CDR1

<400> SEQUENCE: 5

Gly Tyr Ser Phe Ser Asp Tyr Tyr Met His
1               5                   10

<210> SEQ ID NO 6
<211> LENGTH: 17
<212> TYPE: PRT
<213> ORGANISM: Artificial Sequence
<220> FEATURE:
<223> OTHER INFORMATION: Polypeptide anti-CD100 VH CDR2

<400> SEQUENCE: 6

Gln Ile Asn Pro Thr Thr Gly Gly Ala Ser Tyr Asn Gln Lys Phe Lys
1               5                   10                  15

Gly

<210> SEQ ID NO 7
<211> LENGTH: 9
<212> TYPE: PRT
<213> ORGANISM: Artificial Sequence
<220> FEATURE:
<223> OTHER INFORMATION: Polypeptide anti-CD100 VH CDR3

<400> SEQUENCE: 7

Tyr Tyr Tyr Gly Arg His Phe Asp Val
1               5

<210> SEQ ID NO 8
<211> LENGTH: 15
<212> TYPE: PRT
<213> ORGANISM: Artificial Sequence
<220> FEATURE:
<223> OTHER INFORMATION: Polypeptide anti-CD100 VL CDR1

<400> SEQUENCE: 8

Lys Ala Ser Gln Ser Val Asp Tyr Asp Gly Asp Ser Tyr Met Asn
1               5                   10                  15

<210> SEQ ID NO 9
<211> LENGTH: 7
<212> TYPE: PRT
<213> ORGANISM: Artificial Sequence
<220> FEATURE:
<223> OTHER INFORMATION: Polypeptide anti-CD100 VL CDR2

<400> SEQUENCE: 9

Ala Ala Ser Asn Leu Glu Ser
1               5
```

```
<210> SEQ ID NO 10
<211> LENGTH: 9
<212> TYPE: PRT
<213> ORGANISM: Artificial Sequence
<220> FEATURE:
<223> OTHER INFORMATION: Polypeptide anti-CD100 VL CDR3

<400> SEQUENCE: 10

Gln Gln Ser Asn Glu Asp Pro Tyr Thr
1               5

<210> SEQ ID NO 11
<211> LENGTH: 20
<212> TYPE: DNA
<213> ORGANISM: Artificial Sequence
<220> FEATURE:
<223> OTHER INFORMATION: nestin forward

<400> SEQUENCE: 11
cactagaaag caggaaccag                                               20

<210> SEQ ID NO 12
<211> LENGTH: 20
<212> TYPE: DNA
<213> ORGANISM: Artificial Sequence
<220> FEATURE:
<223> OTHER INFORMATION: nestin reverse

<400> SEQUENCE: 12
agatggttca caatcctctg                                               20

<210> SEQ ID NO 13
<211> LENGTH: 20
<212> TYPE: DNA
<213> ORGANISM: Artificial Sequence
<220> FEATURE:
<223> OTHER INFORMATION: Sox2 forward

<400> SEQUENCE: 13
ttgggagggg tgcaaaaaga                                               20

<210> SEQ ID NO 14
<211> LENGTH: 20
<212> TYPE: DNA
<213> ORGANISM: Artificial Sequence
<220> FEATURE:
<223> OTHER INFORMATION: Sox2 reverse

<400> SEQUENCE: 14
cctgcgaagc gcctaacgta                                               20

<210> SEQ ID NO 15
<211> LENGTH: 19
<212> TYPE: DNA
<213> ORGANISM: Artificial Sequence
<220> FEATURE:
<223> OTHER INFORMATION: PLP forward

<400> SEQUENCE: 15
tgagcgcaac ggtaacagg                                                19

<210> SEQ ID NO 16
<211> LENGTH: 22
<212> TYPE: DNA
<213> ORGANISM: Artificial Sequence
<220> FEATURE:
```

```
<223> OTHER INFORMATION: PLP reverse

<400> SEQUENCE: 16
gggagaacac catacattct gg                                            22

<210> SEQ ID NO 17
<211> LENGTH: 21
<212> TYPE: DNA
<213> ORGANISM: Artificial Sequence
<220> FEATURE:
<223> OTHER INFORMATION: Beta-actin forward

<400> SEQUENCE: 17
gctcgtcgtc gacaagggct c                                             21

<210> SEQ ID NO 18
<211> LENGTH: 25
<212> TYPE: DNA
<213> ORGANISM: Artificial Sequence
<220> FEATURE:
<223> OTHER INFORMATION: Beta-actin reverse

<400> SEQUENCE: 18
caaacatgat ctgggtcatc ttctc                                         25
```